US009968535B2

(12) United States Patent
Kitko et al.

(10) Patent No.: US 9,968,535 B2
(45) Date of Patent: May 15, 2018

(54) PERSONAL CARE COMPOSITIONS COMPRISING UNDECYL SULFATES

(75) Inventors: David Johnathan Kitko, Cincinnati, OH (US); Howard David Hutton, III, Oregonia, OH (US); Eric Scott Johnson, Hamilton, OH (US); Thomas Allen Hutchins, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1205 days.

(21) Appl. No.: 12/255,920

(22) Filed: Oct. 22, 2008

(65) Prior Publication Data

US 2009/0155383 A1    Jun. 18, 2009

Related U.S. Application Data

(60) Provisional application No. 61/000,466, filed on Oct. 26, 2007, provisional application No. 61/105,982, filed on Oct. 16, 2008.

(51) Int. Cl.
| *A61K 33/32* | (2006.01) |
| *A61K 8/46* | (2006.01) |
| *A61K 8/27* | (2006.01) |
| *A61Q 5/00* | (2006.01) |
| *A61Q 5/02* | (2006.01) |
| *A61Q 5/12* | (2006.01) |
| *A61Q 19/10* | (2006.01) |

(52) U.S. Cl.
CPC ............... *A61K 8/466* (2013.01); *A61K 8/27* (2013.01); *A61Q 5/006* (2013.01); *A61Q 5/02* (2013.01); *A61Q 5/12* (2013.01); *A61Q 19/10* (2013.01); *A61K 2800/596* (2013.01)

(58) Field of Classification Search
CPC .... A61K 8/466; A61K 8/27; A61K 2800/596; A61Q 5/006; A61Q 5/02; A61Q 5/12; A61Q 19/10
See application file for complete search history.

(56) References Cited

U.S. PATENT DOCUMENTS

| 3,249,550 | A |   | 5/1966 | Metters |
| 3,616,859 | A | * | 11/1971 | Shay et al. ............ 169/44 |
| 4,024,078 | A |   | 5/1977 | Gilbert et al. |
| 4,294,728 | A |   | 10/1981 | Vanlerberghe et al. |
| 4,753,754 | A |   | 6/1988 | Messenger |
| 4,772,424 | A | * | 9/1988 | Greeb ............ 510/125 |
| 4,980,078 | A |   | 12/1990 | Verite et al. |
| 5,077,042 | A |   | 12/1991 | Darkwa et al. |
| RE34,584  | E |   | 4/1994 | Grote |
| 5,440,032 | A |   | 8/1995 | Hirosawa et al. |
| 5,482,543 | A |   | 1/1996 | Bleve et al. |
| 5,580,850 | A |   | 12/1996 | Bigorra |
| 5,610,127 | A |   | 3/1997 | Erilli et al. |
| 5,635,466 | A |   | 6/1997 | Burdon et al. |
| 5,695,748 | A |   | 12/1997 | Francis |
| 5,741,948 | A |   | 4/1998 | Kirishiki et al. |
| 5,750,099 | A |   | 5/1998 | Yoshihara et al. |
| 5,814,323 | A |   | 9/1998 | Lyle |
| 5,906,972 | A |   | 5/1999 | Gabriel et al. |
| 5,942,485 | A |   | 8/1999 | Kemen |
| 5,958,868 | A |   | 9/1999 | Pi Subirana et al. |
| 5,994,595 | A |   | 11/1999 | Onda et al. |
| 6,074,633 | A |   | 6/2000 | Dubief et al. |
| 6,150,322 | A |   | 11/2000 | Singleton et al. |
| 6,207,626 | B1 |   | 3/2001 | Gonzalez et al. |
| 6,399,045 | B1 |   | 6/2002 | Morgan et al. |
| 6,417,408 | B2 |   | 7/2002 | Onda et al. |
| 6,432,420 | B2 |   | 8/2002 | Ellis et al. |
| 6,471,953 | B1 |   | 10/2002 | N'Guyen et al. |
| 6,706,931 | B2 |   | 3/2004 | Edwards |
| 6,849,252 | B1 |   | 2/2005 | Yang |
| 6,884,275 | B2 |   | 4/2005 | Okada et al. |
| 6,946,437 | B2 |   | 9/2005 | Aizawa et al. |
| 7,208,480 | B2 |   | 4/2007 | Williams et al. |
| 7,666,825 | B2 |   | 2/2010 | Wagner et al. |

(Continued)

FOREIGN PATENT DOCUMENTS

| DE | 19534372 A1 | 9/1995 |
| EP |   336803 B1 | 9/1992 |

(Continued)

OTHER PUBLICATIONS

International Search Report dated Mar. 19, 2009, PCT/IB2008/054385.
Bran Luebbe, "Continuous Dilution of Concentrated Alkyl Ether Sulfates", vol. 103-No. 16/1977, 465-466.
XP002545441, Thomson, 1 page.
XP002545442, Thomson, 1 page.

*Primary Examiner* — David Browe
(74) *Attorney, Agent, or Firm* — Carl J. Roof

(57) ABSTRACT

A personal care composition comprising a dermatologically acceptable carrier, and from about 3 wt % to about 40 wt % of at least one undecyl sulfate compound selected from the group consisting of:
a) $R_1-O(CH_2CHR_3O)_y-SO_3M$;
b) $CH_3-(CH_2)_z-CHR_2-CH_2-O(CH_2CHR_3O)_y-SO_3M$; and
c) mixtures thereof;
where $R_1$ represents $CH_3(CH_2)_{10}$, $R_2$ represents H or a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not=0, and M is a mono-valent or di-valent, positively-charged cation.

22 Claims, 1 Drawing Sheet

(56) References Cited

U.S. PATENT DOCUMENTS

| | | |
|---|---|---|
| 2002/0041854 A1 | 4/2002 | Hadasch et al. |
| 2002/0122772 A1 | 9/2002 | Lukenbach et al. |
| 2002/0151738 A1 | 10/2002 | Edwards |
| 2003/0083210 A1 | 5/2003 | Goldberg et al. |
| 2004/0092413 A1 | 5/2004 | Ticktin |
| 2004/0116539 A1 | 6/2004 | Biercevicz |
| 2004/0166071 A1 | 8/2004 | Pfaffernoschke et al. |
| 2004/0166074 A1 | 8/2004 | Darkwa |
| 2004/0235689 A1 | 11/2004 | Sakai et al. |
| 2004/0254253 A1 | 12/2004 | Culeron |
| 2004/0266652 A1 | 12/2004 | Brown et al. |
| 2004/0266656 A1 | 12/2004 | Sakurai |
| 2005/0063934 A1 | 3/2005 | Baker |
| 2005/0166338 A1 | 8/2005 | Arango |
| 2005/0192196 A1 | 9/2005 | Hutton |
| 2005/0241076 A1 | 11/2005 | Bureiko et al. |
| 2006/0024256 A1 | 2/2006 | Wells |
| 2006/0078528 A1 | 4/2006 | Yang et al. |
| 2006/0078529 A1 | 4/2006 | Uchida |
| 2006/0079420 A1 * | 4/2006 | Wagner et al. ............... 510/130 |
| 2006/0083703 A1 | 4/2006 | Torgerson |
| 2006/0083704 A1 | 4/2006 | Torgerson |
| 2006/0128596 A1 | 6/2006 | Koshti et al. |
| 2006/0251605 A1 | 11/2006 | Belmar et al. |
| 2006/0286060 A1 | 12/2006 | Yang |
| 2007/0014823 A1 | 1/2007 | Iwata |
| 2007/0041929 A1 | 2/2007 | Torgerson |
| 2007/0119864 A1 | 5/2007 | Tsai |
| 2007/0207109 A1 | 9/2007 | Peffly |
| 2007/0215642 A1 | 9/2007 | Van der Heijden |
| 2007/0286837 A1 | 12/2007 | Torgerson |
| 2008/0139434 A1 | 6/2008 | Basappa et al. |
| 2008/0153730 A1 | 6/2008 | Tsaur et al. |
| 2009/0221463 A1 | 9/2009 | Kitko |
| 2009/0227482 A1 | 9/2009 | Dong et al. |
| 2009/0324527 A1 | 12/2009 | Okada |
| 2009/0324528 A1 | 12/2009 | Okada |
| 2009/0324529 A1 | 12/2009 | Okada |
| 2009/0324530 A1 | 12/2009 | Yang |
| 2009/0324531 A1 | 12/2009 | Okada |
| 2009/0324532 A1 | 12/2009 | Okada |
| 2010/0143280 A1 | 6/2010 | Yokogi |
| 2010/0143281 A1 | 6/2010 | Okada |
| 2010/0143282 A1 | 6/2010 | Yokogi |
| 2010/0143425 A1 | 6/2010 | Okada |
| 2011/0048449 A1 | 3/2011 | Hutton |
| 2011/0053826 A1 | 3/2011 | Wise |

FOREIGN PATENT DOCUMENTS

| | | |
|---|---|---|
| EP | 0573329 B1 | 7/1997 |
| EP | 0834307 A2 | 4/1998 |
| EP | 1009787 B1 | 6/2000 |
| EP | 1696023 B1 | 4/2008 |
| EP | 1572333 B1 | 5/2008 |
| JP | 56001895 A | 1/1981 |
| JP | 58006209 A | 1/1983 |
| JP | 63143935 A2 | 6/1988 |
| JP | 6107888 A | 4/1994 |
| JP | 07034089 A | 2/1995 |
| JP | 09249900 A | 9/1997 |
| JP | 2002038200 | 2/2002 |
| JP | 2003205039 | 7/2003 |
| JP | 2005113067 A | 4/2005 |
| JP | 2005232118 | 9/2005 |
| JP | 2005255627 A2 | 9/2005 |
| WO | WO98/57615 | 12/1998 |
| WO | WO99/62492 A1 | 12/1999 |
| WO | WO0000170 | 1/2000 |
| WO | WO0040213 A1 | 7/2000 |
| WO | WO0117492 A1 | 3/2001 |
| WO | WO04054693 A1 | 7/2004 |
| WO | WO2005070374 A1 | 8/2005 |
| WO | WO2005074868 A1 | 8/2005 |
| WO | WO2010052092 A1 | 5/2010 |

\* cited by examiner

PERSONAL CARE COMPOSITIONS COMPRISING UNDECYL SULFATES

CROSS REFERENCE TO RELATED APPLICATION

The present application claims priority to U.S. Provisional Application No. 61/000,466, filed on Oct. 26, 2007 and to U.S. Provisional Application No. 61/105,982, filed Oct. 16, 2008.

FIELD OF THE INVENTION

The present invention relates to personal care compositions comprising compounds comprising undecyl sulfates and/or ethoxylated undecyl sulfates (undeceth sulfates).

BACKGROUND OF THE INVENTION

Consumer preferences for personal care compositions such as shampoos and cleansers include fast lathering ("flash lather") and quick, clean rinsing. Currently available products tend to employ conventional surfactants and co-surfactants, including $C_{10}$-$C_{18}$ sulfate blends, which fail to completely meet consumer needs and preferences. For example, lauryl sulfate and lauryl ether sulfate long have been the preferred mainframe surfactants in shampoos and other foaming compositions. Lauryl sulfate provides good lather but may be harsh, causing for example skin and eye irritation, and further may precipitate on dilution leaving surfactant residues as water hardness increases. Lauryl ether sulfate may mitigate harshness and improve hardness sensitivity, but at typical ethoxylation levels, i.e. $(OCH_2CH_2)_3$, or $EO_3$, is a poor latherer and relatively weight inefficient.

There exists a need, therefore, to identify combinations of surfactants and co-surfactants which result in products having flash lather and quick rinsing characteristics, which are not harsh on the skin and are relatively hardness insensitive, and are suitable for use in consumer products.

The present invention meets the aforementioned needs. Applicants unexpectedly have found that compositions comprising undecyl ($C_{11}$) sulfates and undecyl ethoxysulfates ("undeceth sulfates") with low ethoxylation ("EO content") (e.g. singly ethoxylated) have many of the characteristics necessary to fulfill consumer needs and preferences in personal care products. Though previously taught as a member of the group of $C_{10}$-$C_{18}$ sulfate surfactants, the undecyl sulfates were thought to be less suitable for personal care compositions based on studies of lather and foaming properties that were conducted using relatively dilute concentrations (less than 1000 ppm). For example, U.S. Pat. No. 4,732,707 advises that compositions should not contain more than 1% $C_{11}$. Applicants have found, however, that at higher concentrations (for example 3,000 ppm and above), undecyl sulfate and the single ethoxylate of undecyl sulfate (undecyl EO1 sulfate) exhibit properties such as low surface tension and higher critical micelle concentration (CMC). It is believed that these properties contribute to compositions having fast lathering and quick rinsing which is superior to either dodecyl sulfates or lauryl sulfates ($C_{12}$-$C_{16}$ blends, e.g., typically having a ratio of 68/27/5 $C_{12}/C_{14}/C_{16}$), and which are mild and relatively insensitive to water hardness. Such compositions are suitable for use in shampoos, personal cleansers, and other personal care compositions, and may be used in combination with other surfactants, structured surfactants, beauty benefit agents (e.g., conditioner), co-surfactants and/or rheology modifiers to provide desirable consumer benefits.

SUMMARY OF THE INVENTION

Figure 1:
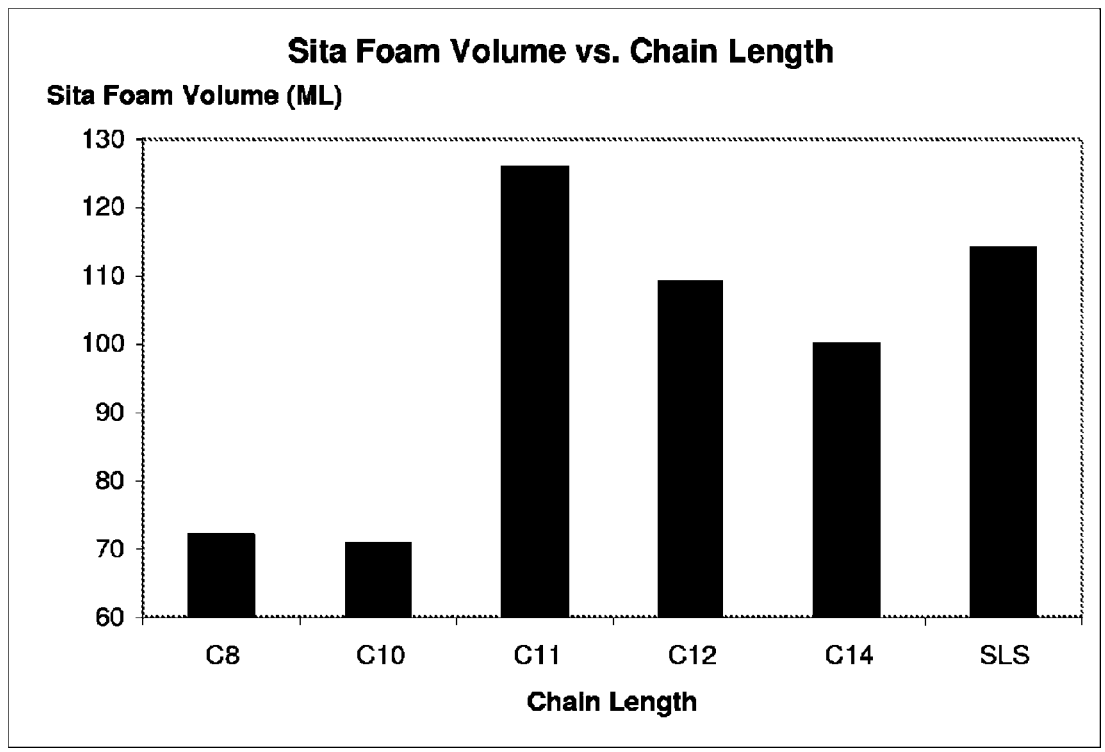
FIG. 1 shows SITA Foam Volume (ml) plotted versus agitation time (s) of the present compositions.

The following describe some non-limiting embodiments of the present invention. According to a first embodiment of the present invention, a personal care composition is provided comprising from about 3 wt % to about 40 wt % of at least one compound selected from the group consisting of:

a) $R_1$—$O(CH_2CHR_3O)_y$—$SO_3M$;
b) $CH_3$—$(CH_2)_z$—$CHR_2$—$CH_2$—$O(CH_2CHR_3O)_y$—$SO_3M$; and
c) mixtures thereof, where $R_1$ represents $CH_3(CH_2)_{10}$, $R_2$ represents H or a hydrocarbon radical comprising 1 to 4 carbon atoms such that the sum of the carbon atoms in z and $R_2$ is 8, $R_3$ is H or $CH_3$, y is 0 to 7, y has an average value of 1 or less, and M is a mono-valent or di-valent, positively-charged cation.

Examples of mono-valent positively charged cations include ammonium, sodium, potassium, triethanolamine cation, and examples of di-valent positively charged cations include magnesium. "Average value" is understood to mean that whereas the composition may comprise molecules having a value of y other than 1, the average value of y of all molecules in the composition is about 1.

According to a second embodiment of the present invention, a personal care composition is provided comprising from about 3 wt % to about 37 wt % of at least one compound of the first embodiment and from about 3 wt % to about 37 wt % of at least one additional anionic surfactant.

According to yet another embodiment of the present invention, a personal care composition is provided comprising from about 3 wt % to about 10 wt % of at least one compound of the first embodiment and from about 10 wt % to about 30 wt % of one or more structured surfactants.

According to yet another embodiment of the present invention, an article of manufacture is provided comprising the composition according to the first embodiment, a pump dispenser suitable for dispensing a foaming composition, and optionally a communication comprising instructions for using the article of manufacture.

According to yet another embodiment, a method is provided for marketing the personal care composition and/or the article of manufacture of the present invention.

These and other aspects and advantages of the present invention will become evident to those skilled in the art from a reading of the following detailed description of the invention.

DETAILED DESCRIPTION OF THE INVENTION

The present invention describes compositions comprising undecyl sulfates and/or ethoxylated undecyl sulfates (undeceth sulfates). The composition of the present invention may be a personal care composition, for example, a cleansing composition and/or shampoo. The composition of the present invention typically is in the form of a liquid, which is understood to include flowable liquids, semi-liquids, creams, lotions and/or gel compositions intended for topical application to mammalian keratinous tissue. The composition may comprise two or more visually distinct phases.

These compositions may have a viscosity of from about 10 cps to about 500,000 cps, where "cps" means centipoise. In some embodiments, the viscosity is from about 10 cps to about 100,000 cps, in one embodiment, the viscosity is from about 10 cps to about 100 cps. In another embodiment, the viscosity of the composition is from about 3,000 cps to about 500,000 cps. In a particular embodiment where the composition is dispensed from a pump foamer, the viscosity is from about 10 cps to about 100 cps. In a particular shampoo embodiment, the viscosity is from about 3,000 cps to about 300,000 cps. Unless otherwise indicated, all measurements are understood to be made at 25° C. and at ambient conditions, where "ambient conditions" means conditions under about one atmosphere of pressure and at about 50% relative humidity.

The compositions of the present invention may produce a stable, fast ("flash") lather, or foam as defined herein. The foam observed in Switch Lather evaluations should provide a Total Lather Volume at least comparable to a Typical Clarifying Shampoo Formulation (defined below in the formulation section), which is about 30% higher than the Typical Conditioning Shampoo Formulation's (defined below in the formulation section) lathering bench mark The compositions of the present invention may rinse rapidly and cleanly after application and lathering switches according to the rinsing protocol for Typical Conditioning Shampoo Formulations discussed herein. Typically the rinsing profile for Typical Conditioning Shampoo Formulations is substantially longer than for Typical Clarifying Shampoo Formulations. The target for a rinsing advantage is therefore to improve a conditioning shampoo's rinse time to be comparable to a Typical Clarifying Shampoo Formulation with at least the same lather volume in use.

Each of the above and additional elements is described herein.

In all embodiments of the present invention, all percentages are by weight of the total composition, unless specifically stated otherwise. All ratios are weight ratios, unless specifically stated otherwise. All ranges are inclusive and combinable. The number of significant digits conveys neither limitations on the indicated amounts nor on the accuracy of the measurements.

"Personal care composition," as used herein, means a composition that may be applied to mammalian keratinous tissue without undue undesirable effects.

"Keratinous tissue," as used herein, means keratin-containing layers disposed as the outermost protective covering of mammals and includes, but is not limited to, skin, hair, scalp and nails.

"Beauty benefit," as used herein in reference to mammalian keratinous tissue includes, but is not limited to cleansing, sebum inhibition, reducing the oily and/or shiny appearance of skin and/or hair, reducing dryness, itchiness and/or flakiness, reducing skin pore size, exfoliation, desquamation, improving the appearance of the keratinous tissue, conditioning, smoothening, etc.

"Beauty benefit agent," as used herein, refers to materials that can be included in the composition to deliver one or more Beauty benefits.

"Skin care actives," or "actives," as used herein, means compounds that, when applied to the skin, provide a benefit or improvement to the skin. It is to be understood that skin care actives are useful not only for application to skin, but also to hair, scalp, nails and other mammalian keratinous tissue.

I. Surfactants

In one embodiment, the composition comprises from about 3 wt % to about 40 wt %, alternatively from about 5 wt % to about 25 wt %, alternatively from about 10 wt % to about 20 wt %, alternatively from about 3 wt % to about 15 wt %, and alternatively from about 3 wt % to about 10 wt %, of an undecyl sulfate compound, understood herein to include straight-chain undecyl sulfates, branched-chain undecyl sulfates, straight-chain undecyl ethoxysulfates, branched-chain undecyl ethoxysulfates, their salts and derivatives, and mixtures thereof.

A. Undecyl Sulfates

The undecyl sulfates of the present invention may comprise straight-chain undecyl sulfates having the formula $R_1$—$O(CH_2CHR_{30})_y$—$SO_3M$, branched-chain undecyl sulfates having the general formula $CH_3$—$(CH_2)_z$—$CHR_2$—$CH_2$—$O(CH_2CHR_{30})_y$—$SO_3M$, or mixtures thereof, where $R_1$ represents $CH_3(CH_2)_{10}$, $R_2$ represents H or a hydrocarbon radical comprising 1 to 4 carbon atoms such that the sum of the carbon atoms in z and $R_2$ is 8, $R_3$ is H or $CH_3$, y is 0 to 7, y has an average value of 1 or less, and M is a mono-valent or di-valent, positively-charged cation. Examples of mono-valent positively charged cations include ammonium, sodium, potassium, triethanolamine cation, and examples of di-valent positively charged cations include magnesium.

"Average value" is understood to mean that whereas the composition may comprise molecules having a value of y other than 1, the average value of y of all molecules in the composition is about 1. The undecyl sulfates may comprise from about 70 wt % to about 90 wt %, and alternatively about 80 wt % of straight-chain undecyl sulfates and about 10 wt % to about 30 wt %, and alternatively about 20 wt %, of branched-chain undecyl sulfates, by weight of the total amount of undecyl sulfates.

The undecyl sulfates of the invention can be prepared by the hydroformylation of 1-decene or internal decenes, for example as described in U.S. Pat. No. 6,706,931, issued Mar. 16, 2004 to Shell Oil Company, to produce linear and branched primary alcohols which are sulfated with $SO_3$ in a falling film reactor and neutralized to make the alkylsulfuric acid salt, e.g. with sodium hydroxide to produce sodium undecyl sulfate. One example of a suitable alcohol is commercially available as NEODOL™ 1 (ex. Shell Oil Co.).

Additionally, the undecyl alcohol can be derived from castor oil via its hydrolysis to obtain ricinoleic acid. Ricinoleic can be pyrolyzed to obtain undecylenic acid. Undecylenic acid can be converted to undecyl alcohol via a series of hydrogenations to obtain undecyl alcohol.

B. Undecyl Alkoxy Sulfates

The undecyl alkoxy sulfates (undeceth sulfates) of the present invention may comprise straight-chain and/or branched-chain undecyl alkoxy sulfates having the general formula $CH_3$—$(CH_2)_z$—$CHR_2$—$CH_2$—$O$—$(CH_2CHR_{30})_y$—$SO_3M$, where $R_2$ represents H or a hydrocarbon radical comprising 1 to 4 carbon atoms such that the sum of the carbon atoms in z and $R_2$ is 8, $R_3$ is H or $CH_3$, y is 1 to 7, y has an average value of 1 or less, and M is a monovalent, positively-charged cation such as ammonium, sodium, potassium and/or triethanolamine cation, etc. or divalent salts of magnesium with two surfactant anions.

The undecyl ethoxylates can be prepared by the addition of one molar equivalent of ethylene oxide or less to the undecyl alcohol in the presence of an alkaline catalyst. The resulting material may comprise from about 30% to about 60% of unethoxylated alcohol, and the remaining mixture will consist of a variety of homologues with EO content ranging from 1 to 7. This mixture can be sulfated in a falling film reactor with $SO_3$ and neutralized with base, e.g. NaOH to produce the sodium undecyl alkoxy sulfates. Additionally, mixtures of the undecyl alcohol and undecyl alkoxylate can be blended together and sulfated as above to produce a mixture of undecyl-based surfactants.

In one embodiment, composition further may be substantially free of additional surfactants, wherein substantially free is understood to mean less than 0.001 wt %. Alternatively, the surfactants in the composition consist essentially of straight-chain undecyl sulfates, branched-chain undecyl sulfates, straight-chain undecyl ethoxy sulfates branched-chain undecyl ethoxylates, their salts and derivatives, and mixtures thereof.

C. Additional Surfactants and Additives

1. Additional Anionic Surfactants

The composition of the present invention may comprise one or more additional surfactants, other than the undecyl sulfates and undecyl ethoxy sulfates, described herein, including those conventionally used in personal care compositions. The additional surfactant(s) may increase the viscosity of the composition and/or may aid in producing lather having more desirable texture, volume, stability and/or other properties. Non-limiting examples of suitable surfactants are disclosed in U.S. Pat. No. 5,624,666, issued to Coffindaffer et al.; in McCutcheon's, *Detergents and Emulsifiers*, North American edition (1986), published by Allured Publishing Corporation; and in McCutcheon's *Functional Materials*, North American Edition (1992).

The composition of the present invention may comprise from about 3 wt % to about 37 wt %, by weight of the composition of additional surfactants.

Additional anionic surfactants suitable for use herein include alkyl and alkyl ether sulfates of the formula $ROSO_3M$ and $RO(C_2H_4O)_xSO_3M$, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats, e.g., coconut oil, palm oil, palm kernel oil, or tallow, or can be synthetic.

Other suitable anionic surfactants include water-soluble salts of the organic, sulfonic acids of the general formula $[R_1—SO_3M]$. $R^1$ being a straight chaining aliphatic hydrocarbon radical having from 13 to 17 carbon atoms, preferably from 13 to 15 carbon atoms. M is a water soluble cation such as ammonium, sodium, potassium, and triethanolamine cation or salts of the divalent magnesium ion with two anionic surfactant anions. These materials are produced by the reaction of $SO_2$ and $O_2$ with suitable chain length normal paraffins ($C_{14}$-$C_{17}$) and are sold commercially as sodium paraffin sulfonates.

Examples of additional anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

2. Co-Surfactants.

Co-surfactants are materials which are combined with the undecyl sulfate surfactant and optionally anionic surfactants to enhance lather volume and/or to modify lather texture. Typically these materials can be selected from a variety of families of structures including, but not limited to, amphoteric, zwitterionic, cationic, and nonionic. They are typically used with anionic surfactants in a weight ratio of 1:20 to 1:4, more preferably in the 1:12 to 1:7 weight ratio.

The composition of the present invention may comprise from about 0.5 wt % to about 10 wt %, alternatively from about 0.5 wt % to about 5 wt %, and alternatively from about 1 wt % to about 3 wt % by weight of the composition of at least one suitable co-surfactant. The co-surfactant may serve to produce faster lather, facilitate easier rinsing, and/or mitigate harshness on the keratinous tissue. The co-surfactant further may aid in producing lather having more desirable texture, volume and/or other properties.

Amphoteric surfactants suitable for use herein include, but are not limited to derivatives of aliphatic secondary and tertiary amines in which the aliphatic radical can be straight or branched chain and wherein one substituent of the aliphatic substituents contains from about 8 to about 18 carbon atoms and one contains an anionic water solubilizing group, e.g., carboxy, sulfonate, sulfate, phosphate, or phosphonate. Examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378, and mixtures thereof. The family of amphoacetates derived from the reaction of sodium chloroacetate with amidoamines to produce alkanoyl amphoacetates are particularly effective, e.g. lauryolamphoacetate, and the like.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof. Also suitable amphoteric surfactants include amidobetaines and amidosulfobetaines, wherein the RCONH (CH$_2$)$_3$ radical, wherein R is a C$_{11}$-C$_{17}$ alkyl, is attached to the nitrogen atom of the betaine are also useful in this invention.

Nonionic co-surfactants typically used in the present composition for enhancing lather volume or texture include water soluble materials like lauryl dimethylamine oxide, cocodimethylamine oxide, cocoamidopropylamine oxide, laurylamidopropyl amine oxide, etc. or alkylpolyethoxylates like laureth-4 to laureth-7 and water insoluble components such as cocomonoethanol amide, cocodiethanol amide, lauroylmonoethanol amide, alkanoyl isopropanol amides, and fatty alcohols like cetyl alcohol and oleyl alcohol, and 2-hydroxyalkyl methyl ethers, etc.

Further suitable materials as co-surfactants herein include 1,2-alkylepoxides, 1,2-alkanediols, branched or straight chain alkyl glyceryl ethers (e.g., as disclosed in EP 1696023A1), 1,2-alkylcyclic carbonates, and 1,2-alkyl cyclicsulfites, particularly those wherein the alkyl group contains 6 to 14 carbon atoms in linear or branched configuration. Other examples include the alkyl ether alcohols derived from reacting C$_{10}$ or C$_{12}$ alpha olefins with ethylene glycol (e.g., hydroxyethyl-2-decyl ether, hydroxyethyl-2-dodecyl ether), as can be made according to the teachings of U.S. Pat. No. 5,741,948; U.S. Pat. No. 5,994,595; U.S. Pat. No. 6,346,509; and U.S. Pat. No. 6,417,408.

Other preferred nonionic surfactants may be selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

In a particular embodiment, the co-surfactant is selected from the group consisting of Cocomonoethanol Amide, Cocoamidopropyl Betaine, Laurylamidopropyl Betaine, Cocobetaine, lauryl betaine, lauryl amine oxide, sodium lauryl amphoacetate; alkyl glyceryl ethers, alkyl-di-glyceryl ethers, 1,2-alkyl cyclic sulfites, 1,2-alkyl cyclic carbonates, 1,2-alkyl-epoxides, alkyl glycidylethers, and alkyl-1,3-di-oxolanes, wherein the alkyl group contains 6 to 14 carbon atoms in linear or branched configuration; 1,2-alkane diols where the total carbon content is from 6 to 14 carbon atoms linear or branched, methyl-2-hydroxy-decyl ethers, hydroxyethyl-2-dodecyl ether, hydroxyethyl-2-decyl ether, and mixtures thereof.

Cationic surfactants may be derived from amines that are protonated at the pH of the formulation, e.g. bis-hydroxyethyl lauryl amine, lauryl dimethylamine, lauroyl dimethyl amidoproplyl amine, cocoylamidopropyl amine, and the like. The cationic surfactants may also be derived from fatty quaternary ammonium salts such as lauryl trimethylammonium chloride and lauroylamidopropyl trimethyl ammonium chloride.

The present personal care composition may comprise two or more phases to make a multiphase person care composition. One phase may comprise traditional personal care components, such as structured surfactants, and the second phase of multiphase personal care compositions of the present invention can comprise a benefit phase.

The benefit phase, when present, is preferably anhydrous and can be substantially free of water. The benefit phase can comprise less than about 5 wt % water, preferable less than 3 wt % water or most preferably less than 1 wt % water. The benefit phase can be substantially free of surfactant. The benefit phase can comprise less than about 5 wt % of surfactant, more preferably less than about 3 wt % of surfactant and most preferably less than about 1 wt % surfactant.

The benefit phase typically comprises hydrophobic moisturizing materials. The benefit phase can be comprised of the components selected from the group consisting of petrolatum, lanolin, hydrocarbon oils such as mineral oil, natural and synthetic waxes such as micro-crystalline waxes, paraffins, ozokerite, lanolin wax, lanolin alcohols, lanolin fatty acids, polyethylene, polybutene, polydecene and perhydrosqualene, volatile or non-volatile organosiloxanes and their derivatives such as dimethicones, cyclomethicones, alkyl siloxanes, polymethylsiloxanes and methylphenylpolysiloxanes, lanolin oil, esters such as isopropyl lanolate, acetylated lanolin, acetylated lanolin alcohols, lanolin alcohol linoleate, lanolin alcohol riconoleate natural and synthetic triglycerides such as castor oil, soy bean oil, sunflower seed oil, maleated soy bean oil, safflower oil, cotton seed oil, corn oil, walnut oil, peanut oil, olive oil, cod liver oil, almond oil, avocado oil, palm oil and sesame oil, castor oil derivatives, sefoses, and combinations thereof.

In a particular embodiment, the benefit phase can comprise a hydrophobic moisturizing material. Hydrophobic moisturizing materials suitable for use in particular multiphase compositions preferably have a Vaughan Solubility Parameter ("VSP") of from about 5 (cal/cm$^3$)$^{1/2}$ to about 15 (cal/cm$^3$)$^{1/2}$, as defined by *Vaughan in Cosmetics and Toiletries*, Vol. 103. Non-limiting examples of hydrophobic moisturizing materials having VSP values ranging from about 5 to about 15 include the following: Cyclomethicone 5.92, Squalene 6.03, Petrolatum 7.33, Isopropyl Palmitate 7.78, Isopropyl Myristate 8.02, Castor Oil 8.90, Cholesterol 9.55, as reported in *Solubility, Effects in Product, Package, Penetration and Preservation*, C. D. Vaughan, Cosmetics and Toiletries, Vol. 103, October 1988.

Structured Surfactants—The composition of the present invention, when in a multiphase form, may comprise structured surfactant that is suitable for application to keratinous tissue such as skin and/or hair. The part of the composition which contains the structured surfactant can comprise in one embodiment at least about 50% of anisotropic phase, and in a different embodiment from about 50% to about 90% of an anisotropic phase. Structured surfactants may comprise anionic, nonionic, cationic, zwitterionic, amphoteric surfactants, soap, and combinations thereof, as disclosed herein and in US 2007/0248562 A1, in combination with a suitable structurant. The choice of a suitable combination of a surfactant and structurant is within the knowledge of one of skill in the art.

Alkylamphoacetates are suitable structured surfactants used in the multiphase compositions herein for improved product mildness and lather. The most commonly used alkylamphoacetates are lauroamphoacetate and cocoamphoacetate. Alkylamphoacetates can be comprised of monoacetates and diacetates. In some types of alkylamphoacetates, diacetates are impurities or unintended reaction products. However, the presence of diacetate can cause a variety of unfavorable composition characteristics when present in amounts over 15% of the alkylamphoacetates.

Suitable nonionic surfactants for use herein are those selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

The structured surfactant may be in the form of a discrete structured domain, visibly distinct from the non-structured domain. Where the composition comprises both a structured and a non-structured phase, the structured domain can enable the incorporation of high levels of skin care actives that are not otherwise emulsified in the composition. In a particular embodiment the structured domain is an opaque structured domain. The opaque structured domain may be a lamellar phase, and may be a lamellar phase that produces a lamellar gel network.

In one embodiment, the structured surfactant is in the form of a lamellar phase, which provides resistance to shear, adequate yield to suspend particles and droplets, desirable rheology characteristics, and/or long term stability. The lamellar phase tends to have a viscosity that minimizes the need for viscosity modifiers.

Non-limiting examples of suitable structurants are described in U.S. Pat. No. 5,952,286, and include unsaturated and/or branched long chain ($C_8$-$C_{24}$) liquid fatty acids or ester derivative thereof, unsaturated and/or branched long chain liquid alcohol or ether derivatives thereof, and mixtures thereof. The structured surfactant also may comprise short chain saturated fatty acids such as capric acid and caprylic acid. Without being limited by theory, it is believed that the unsaturated part of the fatty acid of alcohol or the branched part of the fatty acid or alcohol acts to "disorder" the surfactant hydrophobic chains and induce formation of lamellar phase. Examples of suitable liquid fatty acids include oleic acid, isostearic acid, linoleic acid, linolenic acid, ricinoleic acid, elaidic acid, arichidonic acid, myristoleic acid, palmitoleic acid, and mixtures thereof. Examples of suitable ester derivatives include propylene glycol isostearate, propylene glycol oleate, glyceryl isostearate, glyceryl oleate, polyglyceryl diisostearate and mixtures thereof. Examples of alcohols include oleyl alcohol and isostearyl alcohol. Examples of ether derivatives include isosteareth or oleth carboxylic acid; or isosteareth or oleth alcohol. The structuring agent may be defined as having melting point below about 25° C.

The composition can comprise both an anisotropic and/or an isotropic phase. In a particular embodiment, the structured surfactant is in a visibly distinct phase of the composition.

If present, the composition may comprise a rheology modifier, wherein said rheology modifier comprises cellulosic rheology modifiers, cross-linked acrylates, cross-linked maleic anhydride co-methylvinylethers, hydrophobically modified associative polymers, or a mixture thereof.

An electrolyte, if used, can be added per se to the multiphase composition or it can be formed in situ via the counterions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium chloride, ammonium chloride, sodium or ammonium sulfate. The electrolyte may be added to the structured surfactant phase of the multiphase composition in the amount of from about 0.1 wt % to about 15 wt % by weight, preferably from about 1 wt % to about 6 wt % by weight, more preferably from about 3 wt % to about 6 wt %, by weight of the structured surfactant composition.

In one embodiment of the present invention, the personal care composition comprises a structured surfactant phase comprising a mixture of at least one nonionic surfactant, and an electrolyte. In another embodiment, the surfactant phase can comprise a mixture of surfactants, water, at least one anionic surfactant, an electrolyte, and at least one alkanolamide.

Dermatologically Acceptable Carrier

The personal care compositions of the present invention can also comprise a dermatologically acceptable carrier for the composition. The carrier can be in a wide variety of forms. Non-limiting examples include simple solutions (water or oil based), emulsions, and solid forms (gels, sticks). For example, emulsion carriers can include, but are not limited to, oil-in-water, water-in-oil, water-in-silicone, water-in-oil-in-water, and oil-in-water-in-silicone emulsions.

Depending upon the desired product form, preferred carriers can comprise an emulsion such as oil-in-water emulsions (e.g., silicone in water) and water-in-oil emulsions, (e.g., water-in-silicone emulsions). As will be understood by the skilled artisan, a given component will distribute primarily into either the water or oil phase, depending on the water solubility/dispensability of the component in the composition.

Emulsions according to the present invention can contain an aqueous phase and a lipid or oil. Lipids and oils may be derived from animals, plants, or petroleum and may be natural or synthetic (i.e., man-made). Preferred emulsions can also contain a humectant, such as glycerin.

Emulsions can further comprise from about 0.1 wt % to about 10 wt %, more preferably from about 0.2 wt % to about 5 wt %, of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986). Suitable emulsions may have a wide range of viscosities, depending on the desired product form.

The compositions of the present invention can be in the form of pourable liquids (under Ambient Conditions). The compositions can therefore comprise an aqueous carrier, which is typically present at a level of from about 20 wt % to about 97 wt %, preferably from about 65 wt % to about 90 wt %, alternatively from about 20 wt % to about 95 wt %, preferably from about 60 wt % to about 85 wt %. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

The term "Dermatologically Acceptable," as used herein, means that the compositions or components thereof so described are suitable for use in contact with mammalian keratinous tissue without undue toxicity, incompatibility, instability, allergic response, and/or other adverse effects.

II. Optional Components

The compositions of the present invention may include a broad range of additional components, depending on the product form and its intended use and end benefit. In one embodiment, individual concentrations of such optional components may range from about 0.001 wt % to about 50 wt %, and in another embodiment from about 0.001 wt % to about 10 wt % by weight of the composition.

Non-limiting examples of optional components for use in compositions of the present invention are described in U.S. Pat. No. 6,335,312, issued to Coffindaffer et al. and include cationic polymers, conditioning agents (hydrocarbon oils, fatty esters [e.g., polyol carboxylic acid esters], silicones, insoluble conditioning agents), conventional personal care polymers (deposition polymers, styling polymers, dispersed phase polymers), anti dandruff agents (such as piroctone olamine, water insoluble components such as 3,4,4'-trichlorocarbanilide (trichlosan), triclocarban and zinc pyrithione), antiseborrheic agents, antipsoriasis agents, oxidative dye precursors, developers, oxidizing agents, alkalizing agents, suspending agents, viscosity modifiers, anti-static agents, humectants, emollients, suspending agents, viscosity modifiers, antimicrobial agents, sequestrants, proteins, skin care actives, sunscreens, UV absorbers, vitamins and other aesthetic components such as essential oils, skin sensates, astringents, skin soothing agents, skin healing agents and the like, nonlimiting examples of which include panthenol and derivatives (e.g. ethyl panthenol), pantothenic acid and its derivatives, clove oil, menthol, camphor, eucalyptus oil, eugenol, menthyl lactate, witch hazel distillate, allantoin, bisabalol, dipotassium glycyrrhizinate, derivatives of any of the foregoing and combinations thereof.

Cationic polymers useful herein may include those discussed in US 2007/0207109 A1 and US 2008/0206185 A1, such as synthetic copolymer of sufficiently high molecular weight to effectively enhance the deposition of the conditioning active components of the personal care composition described herein. Combinations of cationic polymer may also be utilized. The average molecular weight of the synthetic copolymers is generally between about 10,000 and about 10 million, preferably between about 100,000 and about 3 million, still more preferably between about 200,000 and about 2 million.

In a further embodiment, the synthetic copolymers have mass charge densities of from about 0.1 meq/gm to about 6.0 meq/gm and more preferably from about 0.5 meq/gm to about 3.0 meq/gm, at the pH of intended use of the personal care composition. The pH will generally range from about pH 3 to about pH 9, and more preferably between about pH 4 and about pH 8.

In yet another embodiment, the synthetic copolymers have linear charge densities from at least about 2 meq/A to about 500 meq/A, and more preferably from about 20 meq/A to about 200 meq/A, and most preferably from about 25 meq/A to about 100 meq/A.

Cationic polymer may be copolymers or homopolymers. In one embodiment, a homopolymer is utilized in the present composition. In another embodiment, a copolymer is utilized in the present composition. In another embodiment a mixture of a homopolymer and a copolymer is utilized in the present composition. In another embodiment, a homopolymer of a naturally derived nature, such as cellulose or guar polymer discussed herein, is combined with a homopolymer or copolymer of synthetic origin, such as those discussed below.

Homopolymers—Non-crosslinked cationic homopolymers of the following monomers are also useful herein: 3-acrylamidopropyltrimethylammonium chloride (APTAC), diallyldimethylammonium chloride (DADMAC), [(3-methylacrylolyamino)propyl]trimethylammonium chloride (MAPTAC), 3-methyl-1-vinylimidazolium chloride (QVI); [2-(acryloyloxy)ethyl]trimethylammonium chloride and [2-(acryloyloxy)propyl]trimethylammonium chloride.

Copolymers—copolymer may be comprises of two cationic monomer or a nonionic and cationic monomers.

Nonionic Monomer Unit

A copolymer suitable for use herein comprises a nonionic monomer unit represented by the following Formula I:

I.

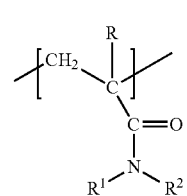

Formula I where R is H or $C_{1-4}$ alkyl; and $R^1$ and $R^2$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl.

In one embodiment, nonionic monomer unit is acrylamide (AM), i.e., where R, $R^1$, and $R^2$ are all H as shown below in formula II:

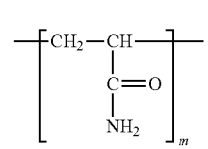

Formula II where m is equal to 1.

Another preferred nonionic monomer unit is methacrylamide (MethAM), i.e., where R is $C_1$ alkyl, and $R^1$ and $R^2$ are each H respectively:

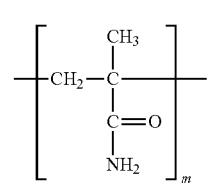

Formula III where m is equal to 1.

However, the other acrylamide derivatives within the scope of the formula set out above are also contemplated to be suitable where polyacrylamide and copolymers using acrylamide monomers are useful.

The nonionic monomer portion of the copolymer may be present in an amount from about 50 wt % to about 99.5 wt % by weight of the total copolymer. Preferably, this amount is from about 70 wt % to about 99 wt %, still more preferably from about 80 wt % to about 99 wt % by weight of copolymer.

Cationic Monomer Unit

The copolymers may also comprise a cationic monomer unit represented by Formula IV:

Formula IV

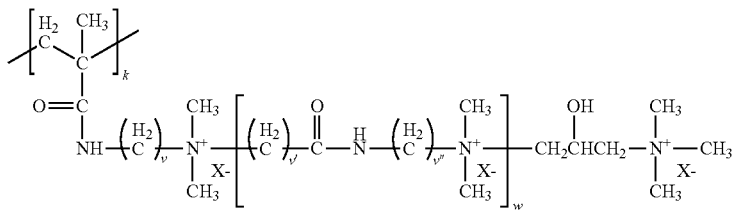

where k=1, each of v, v', and v" is independently an integer of from 1 to 6, w is zero or an integer of from 1 to 10, and X⁻ is an anion.

In one embodiment, a structure is present where k=1, v=3 and w=0 and X⁻ is Cl⁻ according to Formula IV, above, to form the following structure:

Formula V

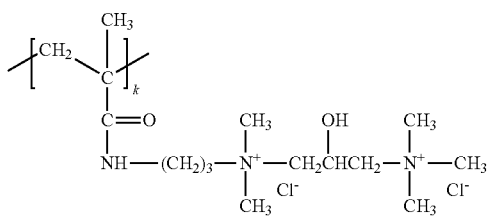

The above structure may be referred to as diquat.

Yet another embodiment is achieved by the structure formed wherein k=1, v and v" are each 3, v'=1, w=1, and X⁻ is Cl⁻ according to Formula IV, such as:

Formula VI

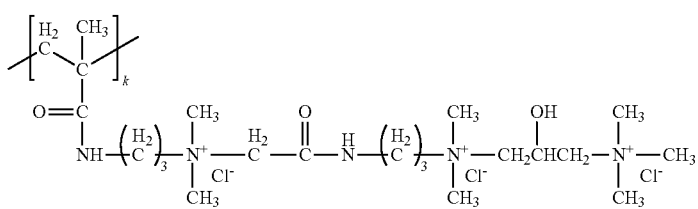

The above structure may be referred to as triquat.

Suitable cationic monomers can be made by, for example, the methods described in U.S. Patent Application Publication No. 2004/0010106 A1.

Cellulose or Guar Cationic Deposition Polymers

The personal care compositions may also comprise cellulose or guar cationic deposition polymers. Generally, such cellulose or guar cationic deposition polymers may be present at a concentration from about 0.05% to about 5%, by weight of the composition. Suitable cellulose or guar cationic deposition polymers have a molecular weight of greater than about 5,000. Additionally, such cellulose or guar deposition polymers have a charge density from about 0.5 meq/g to about 4.0 meq/g at the pH of intended use of the personal care composition, which pH will generally range from about pH 3 to about pH 9, preferably between about pH 4 and about pH 8. The pH of the compositions is measured neat.

In one embodiment of the invention, the cationic polymers are derivatives of Hydroxypropyl Guar, examples of which include polymers known via the INCI nomenclature as Guar Hydroxypropyltrimonium Chloride, such as the products sold under the name Catinal CG-100, Catinal CG-200 by the company Toho, Cosmedia Guar C-261N, Cosmedia Guar C-261N, Cosmedia Guar C-261N by the company Cognis, DiaGum P 5070 by the company Freedom Chemical Diamalt, N-Hance Cationic Guar by the company Hercules/Aqualon, Hi-Care 1000, Jaguar C-17, Jaguar C-2000, Jaguar C-13S, Jaguar C-14S, Jaguar Excel by the company Rhodia, Kiprogum CW, Kiprogum NGK by the company Nippon Starch.

Anti-Dandruff Actives—The compositions of the present invention may also contain an anti-dandruff agent. Suitable, non-limiting examples of anti-dandruff particulates include: pyridinethione salts, zinc-containing layered material, azoles, such as ketoconazole, econazole, and elubiol, selenium sulfide, particulate sulfur, salicylic acid and mixtures thereof. A typical anti-dandruff particulate is pyridinethione salt. Such anti-dandruff particulate should be physically and chemically compatible with the components of the composition, and should not otherwise unduly impair product stability, aesthetics or performance.

Pyridinethione Salts

Pyridinethione anti-dandruff particulates, especially 1-hydroxy-2-pyridinethione salts, are suitable particulate anti-dandruff agents for use in compositions of the present invention. The concentration of pyridinethione anti-dandruff particulate typically ranges from about 0.01 wt % to about 5 wt %, by weight of the composition, generally from about 0.1 wt % to about 3 wt %, commonly from about 0.1 wt % to about 2 wt %. Suitable pyridinethione salts include those formed from heavy metals such as zinc, tin, cadmium, magnesium, aluminum and zirconium, generally zinc, typically the zinc salt of 1-hydroxy-2-pyridinethione (known as "zinc pyridinethione" or "ZPT"), commonly 1-hydroxy-2-pyridinethione salts in platelet particle form, wherein the particles have an average size of up to about 20μ, typically up to about 5μ, commonly up to about 2.5μ. Salts formed from other cations, such as sodium, may also be suitable. Pyridinethione anti-dandruff agents are described, for example, in U.S. Pat. No. 2,809,971; U.S. Pat. No. 3,236, 733; U.S. Pat. No. 3,753,196; U.S. Pat. No. 3,761,418; U.S. Pat. No. 4,345,080; U.S. Pat. No. 4,323,683; U.S. Pat. No. 4,379,753; and. U.S. Pat. No. 4,470,982.

Anti-Microbial Actives

In addition to the anti-dandruff active selected from polyvalent metal salts of pyrithione, the present invention may further comprise one or more anti-fungal or anti-microbial actives in addition to the metal pyrithione salt actives.

Additional suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Typical anti-microbials include itraconazole, ketoconazole, selenium sulphide and coal tar.

Azoles

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, typically from about 0.1% to about 3%, and commonly from about 0.3% to about 2%, by weight of the composition. Especially common for use herein is ketoconazole.

Selenium Sulfide

Selenium sulfide is a particulate anti-dandruff agent suitable for use in the anti-microbial compositions of the present invention, effective concentrations of which range from about 0.1 wt % to about 4 wt %, by weight of the composition, typically from about 0.3 wt % to about 2.5 wt %, commonly from about 0.5 wt % to about 1.5 wt %. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 µm, as measured by forward laser light scattering device (e.g. Malvern 3600 instrument), typically less than 10 µm. Selenium sulfide compounds are described, for example, in U.S. Pat. No. 2,694,668; U.S. Pat. No. 3,152,046; U.S. Pat. No. 4,089,945; and U.S. Pat. No. 4,885,107.

Sulfur

Sulfur may also be used as a particulate anti-microbial/anti-dandruff agent in the anti-microbial compositions of the present invention. Effective concentrations of the particulate sulfur are typically from about 1 wt % to about 4 wt %, by weight of the composition, typically from about 2 wt % to about 4 wt %.

Keratolytic Agents

The present invention may further comprise one or more keratolytic agents such as Salicylic Acid.

Zinc-Containing Layered Material

In an embodiment of the present invention, the composition may include an effective amount of a zinc-containing layered material. Preferred embodiments of the present invention include from about 0.001% to about 10% of a zinc-containing layered material; more preferably from about 0.01% to about 7%; more preferably still from about 0.1% to about 5%.

Examples of zinc-containing layered materials useful in certain embodiments of the present invention include the following:

Zinc-containing layered structures are those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLM's) may have zinc incorporated in the layers and/or be components of the gallery ions.

Many ZLM's occur naturally as minerals. Common examples include hydrozincite (zinc carbonate hydroxide), basic zinc carbonate, aurichalcite (zinc copper carbonate hydroxide), rosasite (copper zinc carbonate hydroxide) and many related minerals that are zinc-containing. Natural ZLM's can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLM's, which are often, but not always, synthetic, is layered doubly hydroxides, which are generally represented by the formula $[M^{2+}_{1-x}M^{3+}_x(OH)_2]^{x+}A^{m-}_{x/m} \cdot nH_2O$ and some or all of the divalent ions ($M^{2+}$) would be represented as zinc ions (Crepaldi, E L, Pava, P C, Tronto, J, Valim, J B J. Colloid Interfac. Sci. 2002, 248, 429-42).

Yet another class of ZLM's can be prepared called hydroxy double salts (Morioka, H., Tagaya, H., Karasu, M, Kadokawa, J, Chiba, K Inorg. Chem. 1999, 38, 4211-6). Hydroxy double salts can be represented by the general formula $[M^{2+}_{1-x}M^{2+}_{1+x}(OH)_{3(1-y)}]^+A^{n-}_{(1=3y)/n} \cdot nH_2O$ where the two metal ion may be different; if they are the same and represented by zinc, the formula simplifies to $[Zn_{1+x}(OH)_2]^{2x+}2x\,A^- \cdot nH_2O$. This latter formula represents (where x=0.4) common materials such as zinc hydroxychloride and zinc hydroxynitrate. These are related to hydrozincite as well wherein a divalent anion replace the monovalent anion. These materials can also be formed in situ in a composition or in or during a production process.

These classes of ZLM's represent relatively common examples of the general category and are not intended to be limiting as to the broader scope of materials which fit this definition.

Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA).

Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice It has been found, in accordance with an embodiment of the present invention, that anti-dandruff efficacy can be dramatically increased in topical compositions by the combination of an effective amount of a zinc-containing layered material wherein the zinc-containing layered material has a specified zinc lability within a surfactant system. Zinc lability is a measure of the chemical availability of zinc ion. Soluble zinc salts that do not complex with other species in solution have a relative zinc lability, by definition, of 100%. The use of partially soluble forms of zinc salts and/or incorporation in a matrix with potential complexants generally lowers the zinc lability substantially below the defined 100% maximum.

Labile zinc is maintained by choice of an effective zinc-containing layered material or formation of an effective zinc-containing layered material in-situ by known methods.

It has been found, in accordance with an embodiment of the present invention, that anti-dandruff efficacy can be dramatically increased in topical compositions by the use of polyvalent metal salts of pyrithione, such as zinc pyrithione, in combination with zinc-containing layered materials. Therefore an embodiment of the present invention provides topical compositions with improved benefits to the skin and scalp (e.g., improved antidandruff efficacy).

An embodiment of the present invention provides a stable composition for zinc-containing layered material dispersion where the zinc source resides in a particulate form. It has been shown to be challenging to formulate aqueous systems containing a zinc-containing layered material, due to the zinc-containing layered material's unique physical and chemical properties. Zinc-containing layered material may have a high density (approximately 3 g/cm$^3$), and needs to be evenly dispersed throughout the product and so it will not aggregate or settle. Zinc-containing layered material also has a very-reactive surface chemistry as well as the propensity to dissolve in systems with pH values below 6.5.

A zinc-containing layered material with a solubility of less than 25% will have a measurable % soluble zinc value below a threshold value determined by the weight percent and molecular weight of the zinc compound. The theoretical threshold value can be calculated by the following equation:

$$\frac{0.25 * \text{wt. \% Zn Compound in Composition} * \text{moles of Zincin Compound} * 65.39 \text{ (MW of Zn)}}{\text{MW of Zn Compound}}$$

In an embodiment of the present invention, wherein the composition comprises a ZLM, the pH may be greater than about 6.5; further, the pH may be in a range from about 6.5 to about 12, preferably from about 6.8 to about 9.5, more preferably from about 6.8 to about 8.5.

Particle Size of ZLM

In an embodiment of the present invention, it is has been found that a smaller particle size is inversely proportional to relative zinc lability D(90) is the particle size which corresponds to 90% of the amount of particles are below this size. In an embodiment of the present invention, the zinc-containing layered material may have a particle size distribution wherein 90% of the particles are less than about 50 microns. In a further embodiment of the present invention, the zinc-containing layered material may have a particle size distribution wherein 90% of the particles are less than about 30 microns. In yet a further embodiment of the present invention, the zinc-containing layered material may have a particle size distribution wherein 90% of the particles are less than about 20 microns.

Surface Area of ZLM

In an embodiment of the present invention, there may be a direct relationship between surface area and relative zinc lability.

Increased particle surface area generally increases zinc lability due to kinetic factors. Particulate surface area can be increased by decreasing particle size and/or altering the particle morphology to result in a porous particle or one whose overall shape deviates geometrically from sphericity.

In an embodiment of the present invention, the basic zinc carbonate may have a surface area of greater than about 10 m$^2$/gm. In a further embodiment, the basic zinc carbonate may have a surface area of greater than about 20 m$^2$/gm. In yet a further embodiment of the present invention, the basic zinc carbonate may have a surface area of greater than about 30 m$^2$/gm.

Coordinating Compound Having a Log Zn Binding Constant

In a further embodiment of the present invention, the composition further comprises a coordinating compound with a Log Zn binding constant in a range sufficient to maintain zinc bioavailability. Preferably, such a coordinating compound has a Log Zn binding constant less than about 6, preferably less than about 5, more preferable less than about 4, and greater than about −0.5. Preferably such a coordinating compound is an organic acid, strong mineral acid, or coordinating species. Preferred examples of such coordinating compounds include the following (respective Log Zn Binding Constant indicated in parenthesis): EDTA (16.5), EDDS (13.5), EDDA (11.1), NTA (10.7), Xylenol Orange (10.3), Cysteine (9.1), Cystine (6.7), Aspartic Acid (Aspartate) (5.9), Glycine (5.0), Citric Acid (Citrate) (4.8), Glutamic Acid (4.5), Methionine (4.4), Arginine (4.2), Carbonic Acid (Carbonate) (3.9), Ornithine (3.8), Tatronic Acid (Tartrate) (3.2), Malic Acid (Malate) (2.9), Malonic Acid (Malonate) (2.9), Tartaric Acid (Tartrate) (2.7), Adipic Acid (Adipate) (2.6), Phosphoric Acid (Phosphate) (2.4), Phthalic Acid (Phthalate) (2.2), Glycolic Acid (Glycolate) (2.0), Lactic Acid (Lactate) (1.9), Succinic Acid (Succinate) (1.8), Acetic Acid (Acetate) (1.0), Sulfuric Acid (Sulfate) (0.9), Boric Acid (Borate) (0.9), Formic Acid (Formate) (0.6), Chloride (−0.3).

Pyrithione or a Polyvalent Metal Salt of Pyrithione

In an embodiment, the present invention may comprise pyrithione or a polyvalent metal salt of pyrithione. Any form of polyvalent metal pyrithione salts may be used, including platelet and needle structures. Preferred salts for use herein include those formed from the polyvalent metals magnesium, barium, bismuth, strontium, copper, zinc, cadmium, zirconium and mixtures thereof, more preferably zinc. Even more preferred for use herein is the zinc salt of 1-hydroxy-2-pyridinethione (known as "zinc pyrithione" or "ZPT"); more preferably ZPT in platelet particle form, wherein the particles have an average size of up to about 20 μm, preferably up to about 5 μm, more preferably up to about 2.5 μm.

Pyridinethione anti-microbial and anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

It is further contemplated that when ZPT is used as the anti-microbial particulate in the anti-microbial compositions herein, that an additional benefit of hair growth or re-growth may be stimulated or regulated, or both, or that hair loss may be reduced or inhibited, or that hair may appear thicker or fuller.

Zinc pyrithione may be made by reacting 1-hydroxy-2-pyridinethione (i.e., pyrithione acid) or a soluble salt thereof with a zinc salt (e.g. zinc sulfate) to form a zinc pyrithione precipitate, as illustrated in U.S. Pat. No. 2,809,971.

Preferred embodiments include from about 0.01 wt % to about 5 wt % of a pyrithione or polyvalent metal salt of a pyrithione; more preferably from about 0.1 wt % to about 2 wt %.

In embodiments having a zinc-containing layered material and a pyrithione or polyvalent metal salt of pyrithione, the ratio of zinc-containing layered material to pyrithione or a polyvalent metal salt of pyrithione is preferably from 5:100 to 10:1; more preferably from about 2:10 to 5:1; more preferably still from 1:2 to 3:1.

Additional Anti-Microbial Actives

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, elubiol and zinc pyrithione combinations, elubiol and salicylic acid combinations, octopirox and climbasole combinations, and salicylic acid and octopirox combinations, and mixtures thereof.

Other useful components which could be utilized herein include hair containing agents. Non-limiting examples of insoluble hair conditioning agents, silicone conditioning agents, and other useful optional components are described in U.S. Pat. No. 6,221,817, issued to Guskey et al., Furthermore, additional components can include sugar amines (e.g., N-acetylglucosamine), vitamin $B_3$ compounds, sodium dehydroacetate, dehydroacetic acid and its salts, phytosterols, soy derivatives (e.g., equol and other isoflavones), niacinamide, phytantriol, franesol, bisabolol, salicylic acid compounds, hexamidines, dialkanoyl hydroxyproline compounds, flavonoids, N-acyl amino acid compounds, retinoids (e.g., retinyl propionate), water-soluble vitamins, ascorbates (e.g., vitamin C, ascorbic acid, ascorbyl glucoside, ascorbyl palmitate, magnesium ascorbyl phosphate, sodium ascorbyl phosphate), particulate materials, sunscreen actives, anti-cellulite agents, butylated hydroxytoluene, butylated hydroxyanisole, their derivatives, and combinations thereof dyes, nonvolatile solvents or diluents (water soluble and insoluble), pearlescent aids, foam boosters, pediculocides, pH adjusting agents, perfumes, particles (e.g., organic, inorganic) preservatives, chelants, chelating agents, proteins, UV absorbers, pigments, other amino acids, and other vitamins.

For instance, the compositions of the present invention may comprise one or more vitamins and/or amino acids such as: water soluble vitamins such as vitamin $B_1$, $B_2$, $B_6$, $B_{12}$, C, pantothenic acid, pantothenyl ethyl ether, panthenol, biotin, and their derivatives, water soluble amino acids such as asparagine, alanine, glutamic acid and their salts, water insoluble vitamins such as vitamin A, D, E, and their derivatives, water insoluble amino acids such as tyrosine, tryptophan, and their salts.

The compositions of the present invention may also contain one or more pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocyanine, botanical, natural colors, including: water soluble components such as those having C. I. Names. The compositions of the present invention may also contain antimicrobial agents which are useful as cosmetic biocides and antidandruff agents including: water soluble components Furthermore, the composition can comprise other peptides, such as those disclosed in U.S. Pat. No. 6,492,326, issued Dec. 10, 2002, to Robinson et al. (e.g., pentapeptides such as lys-thr-thr-lys-ser, and derivatives thereof). Suitable pentapeptide derivatives include palmitoyl-lys-thr-thr-lys-ser, available from Sederma, France. Another optional dipeptide that can be used in the composition herein is carnosine. As used herein, the term "peptide" is broad enough to include one or more peptide, one or more peptide derivatives, and combinations thereof.

Any other suitable optional component can also be included in the personal care composition of the present invention, such as those ingredients that are conventionally used in given product types. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

III. Methods of Making

Any suitable method of making the personal care compositions of the present invention may be used. In one embodiment, undecyl-based surfactant is blended with the other components of the personal care compositions, according to standard methods known in the art. The typical procedure used for a clarifying shampoo would be to combine the undecyl sulfate paste or undeceth sulfate paste or mixtures thereof with water, add the desired water soluble co-surfactant and finish the composition by the addition of preservatives, pH control agents, perfume, and salts to obtain the target physical properties. If a water insoluble co-surfactant is desired the surfactant and water mixture can be heated to a suitable temperature to facilitate its incorporation. If a rheology modifier is desired it can be added to the resulting surfactant mixture prior the finishing step.

In the case of conditioning shampoos, typically the surfactant paste is combined with the co-surfactant as above and diluted with water to a target level commensurate to achieving the final activity. Rheology modifiers can be added at this point followed by conditioning agents, e.g. silicones or silicone emulsions or other oils, cationic polymers from polymer premixes, perfumes, pearlizing agents or opacifiers, perfumes, and preservatives. Appropriate mixing steps to insure homogeneity are used as needed. The product is finished by the addition of pH control agents, hydrotropes, and salts to the desired physical properties.

In a particular embodiment, the personal care composition comprises a surfactant wherein said surfactant consists essentially of undecyl-based surfactant. The sodium undecyl sulfate can be prepared as an isotropic, fluid paste in a falling film reactor with typically available neutralization equipment at or above 37% activity. The sodium undeceth (1) sulfate can be prepared similarly at about 32% activity without encountering the presence of cubic gel phases which give rise to settling and inhomogeneous systems and unsuitability for making personal care products. These pastes can be combined with the appropriate co-surfactant to allow low viscosity products (less than 100 cps at 25° C.) to be made that provide exceptionally high performing products for lather and cleaning from pump foamers.

IV. Methods of Use

The compositions of the present invention may be used for cleansing and conditioning mammalian keratinous tissue such as hair and/or skin, and provide rapid lathering and/or rinseability. The method for cleansing and conditioning the hair may comprise the steps of: a) wetting the hair with water, b) applying an effective amount of the personal cleansing composition, such as a shampoo composition, to the hair, and c) rinsing the composition from the hair using water. These steps can be repeated as many times as desired to achieve the desired cleansing and conditioning benefit.

According to yet another embodiment, a method is provided for providing a benefit to mammalian keratinous tissue, comprising the step of applying the composition of the present invention to keratinous tissue in need of regulating.

The present invention provides for a method for regulating the condition of mammalian keratinous tissue, comprising the step of applying one or more compositions described herein to mammalian keratinous tissue in need of regulation. The application of the present compositions may occur through a variety of means, non-limiting examples of which include using the palms of the hands and/or fingers, a delivery enhancement device (understood to include any device that increases the amount of composition and/or active ingredient applied to and/or into the keratinous tissue relative to the amount of active ingredient that is delivered without using the device), a temperature-change element, a substrate, an implement (e.g., a sponge, loofah, puff, pad, substrate, etc.), and combinations thereof.

According to yet another embodiment of the present invention, a method of providing a stable personal care foam is provided, comprising the step of dispensing from a suitable pump dispenser a composition according to the first embodiment. Non-limiting examples of suitable pump dispensers include those described in WO 2004/078903, WO 2004/078901, and WO 2005/078063.

The composition may have a viscosity prior to dispensing from a pump foamer of from about 10 to about 100 centipoise (cps) at 25° C., in another embodiment from about 10 to about 60 cps at 25° C., and in another embodiment from about 10 to about 30 cps at 25° C.

The amount of the composition applied, the frequency of application and the period of use will vary widely depending upon the purpose of application, the level of components of a given composition and the level of regulation desired. For example, when the composition is applied to the hair, effective amounts generally range from about 1 g to about 50 g, preferably from about 1 g to about 20 g or alternatively, an amount sufficient to contact most or all of the hair with the composition. When the composition is applied to the skin, an effective amount may comprise from about 0.01 g composition/cm$^2$ to about 1 g composition/cm$^2$ of keratinous tissue.

V. Article of Commerce

The present invention provides for an article of commerce comprising one or more compositions described herein, and a communication directing a consumer to apply the composition to keratinous tissue to produce a cleansing effect, a benefit to keratinous tissue such as skin and/or hair, a rapidly lathering foam, a rapidly rinsing foam, a clean rinsing foam, and combinations thereof. The communication may be printed material attached directly or indirectly to packaging that contains the composition. Alternatively, the communication may be an electronic or a broadcast message that is associated with the article of manufacture. Alternatively, the communication may describe at least one possible use, capability, distinguishing feature and/or limitation of the article of manufacture.

EXAMPLES

Example 1—Surfactant Combination Screening Evaluations (Sita Foam Tester)

This example demonstrates the flash foam tendency of the surfactant under mild agitation conditions.

Sita Test Method

The SITA Foam Tester R-2000 is used to measure inherent foamability of products and/or specific surfactants and/or other raw materials. To measure the inherent foamability of surfactants and active materials for shampoo application, the following procedure is followed:

Stock Solution: A 500 ml stock solution of surfactant with 0.1% w/v NaCl is prepared at a concentration to represent a 1:10 dilution of shampoo with reverse osmosis (RO) water (either at ambient temperature or at elevated temperature). When all solids are dissolved and the sample has reached appropriate temperature, pH is adjusted to 7.0+/−0.5 using either HCl or NaOH. Finally, a hardness stock solution is spiked into the sample to add 6 gpg (3:1 Ca:Mg) water hardness (representative of average North American water conditions). As soon as the hardness solution is added, the sample mixes for 1 minute (via magnetic stir plate), then is immediately transferred to the SITA Foam Tester R-2000 sample reservoir. Immediately, upon transferring the test solution to SITA reservoir, the SITA test is started.

SITA Foam Tester R-2000: Prior to each sample tested on the SITA, the instrument must be thoroughly cleaned—including the sample reservoir, the sample line, agitation vessel, and rotor. The SITA computer software is used to control the following agitation and measurement cycles: The sample fills to 300 ml, stirs at 500 rpm for 20 seconds preceding each of 9 measuring cycles. Foam volume is measured between each agitation cycle via patented sensor technology (conductive probes situated to identify the "foam hill" enable the device to calculate a surface profile and thus calculate foam volume).

SITA Foam Volume (ml) is plotted versus agitation time (s) to show the overall foam generation profile of a given sample. The 180s time point is recorded as a description of the sample's inherent foamability.

Measurements of the present composition are reported in FIG. 1, which are made at 16% surfactant concentration, at 40° C. due to solubility limitations of $C_{14}$ at lower temperature.

In the Sita foam tester evaluation, if a volume of 100 ml of foam is produced according to the method described at typical in-use concentrations of surfactant for shampoos, then the surfactant is deemed suitable for shampoo compositions. Although, $C_{12}$ and SLS (sodium lauryl sulfate, a blend of $C_{12}/C_{14}/C_{16}$ chain lengths in a ratio of about 68/27/5) are shown to be suitable for shampoo compositions, FIG. 1 demonstrates that the undecyl sulfate has an unexpected, higher lather profile versus chain lengths $C_8$-$C_{14}$ and SLS.

Example 2—Sita Foam Testing with Co-Surfactants*

TABLE 1

| | 1 Wt. % (comparative) | 2 Wt. % | 3 Wt. % | 4 Wt. % | 5 Wt. % | 6 Wt. % | 7 Wt. % |
|---|---|---|---|---|---|---|---|
| Anionic Surfactants | | | | | | | |
| SLS (sodium lauryl sulfate) | 16 | — | — | — | — | — | — |
| NaUndecyl sulfate | — | 16 | 14 | 14 | 14 | 14 | 14 |
| Co-Surfactants | | | | | | | |
| 1,2-decanediol | — | — | 2 | — | — | — | — |
| methyl 2-hydroxy decyl ether | — | — | — | 2 | — | — | — |
| 1,2 decyl carbonate | — | — | — | — | 2 | — | — |
| hydroxy ethyl 2-dodecyl ether | — | — | — | — | — | 2 | — |
| 1,2-decyl sulphite (cyclic) | — | — | — | — | — | — | 2 |
| Sita Foam Volume | 115 | 126 | 132 | 142 | 140 | 132 | 142 |

Example 2 demonstrates that undecyl-sulfate provides higher flash lather than lauryl-sulfate. Furthermore, the co-surfactants disclosed herein even further improve the flash lather of undecyl-sulfate, enabling superior foam volumes.

*This example was carried out at 40° C.

Example 3—Sita Screening for Flash Lather*

TABLE 2

| | 8 Wt % | 9 Wt % | 10 Wt % | 11 Wt % | 12 Wt % | 13 Wt % | 14 Wt % | 15 Wt % | 16 Wt % | 17 Wt % |
|---|---|---|---|---|---|---|---|---|---|---|
| Anionic Surfactants | | | | | | | | | | |
| Sodium laurel sulfate | 6 | 6 | 6 | — | — | — | — | — | — | — |
| Sodium laureth(1) sulfate (SLE(1)S) | — | — | 6 | — | — | 6 | — | 12 | — | — |
| Sodium laureth(3)sulfate (SLE(3)S) | 6 | — | — | — | 6 | — | 12 | — | — | — |
| Undecyl sulfate | — | — | — | 6 | 6 | 6 | — | — | 12 | — |
| Undeceth(1) Sulfate | — | 6 | — | 6 | — | — | — | — | — | 12 |
| Co-Surfactants | — | — | — | — | — | — | — | — | — | — |
| Cocoamido propyl betaine (CAPB) | 1 | 1 | 1 | 1 | 1 | 1 | 1 | 1 | 1 | 1 |
| Cocomonoethanolamide (CMEA) | 0.5 | 0.5 | 0.5 | 0.5 | 0.5 | 0.5 | 0.5 | 0.5 | 0.5 | 0.5 |
| Sita Foam Volume, ml | 106 | 110 | 104 | 127 | 113 | 116 | 98 | 102 | 127 | 125 |

As this data from Example 3 shows, Undecyl sulfate and Undeceth (1) Sulfate provide better flash lather than the lauryl-based materials with conventional foam boosters, cocoamido propyl betaine (CAPB) and cocomonoethanolamide (CMEA).

*This example was carried out at room temperature (25° C.).

Example 4—Sita Foam Testing* with Anionics Plus Co-Surfactants

TABLE 3

| | 18 Wt % | 19 Wt % | 20 Wt % | 21 Wt % | 22 Wt % | 23 Wt % | 24 Wt % | 25 Wt % | 26 Wt % | 27 Wt % | 28 Wt % | 29 Wt % | 30 Wt % | 31 Wt % | 32 Wt % | 33 Wt % | 34 Wt % | 35 Wt % |
|---|---|---|---|---|---|---|---|---|---|---|---|---|---|---|---|---|---|---|
| Anionic Surfactants | | | | | | | | | | | | | | | | | | |
| SLS | 8 | — | 8 | 8 | 8 | 8 | 8 | 8 | 8 | 8 | — | — | — | — | — | — | — | — |
| SLE(3)S | 4 | — | 4 | 4 | 4 | 4 | 4 | 4 | 4 | 4 | — | — | — | — | — | — | — | — |
| Undecyl Sulfate | — | 8 | — | — | — | — | — | — | — | — | 8 | 8 | 8 | 8 | 8 | 8 | 8 | 8 |
| Undeceth(1) Sulfate | — | 4 | — | — | — | — | — | — | — | — | 4 | 4 | 4 | 4 | 4 | 4 | 4 | 4 |
| Co-Surfactant | | | | | | | | | | | | | | | | | | |
| CMEA | 1.2 | 1.2 | — | — | — | — | — | — | — | — | — | — | — | — | — | — | — | — |
| 1,2-decanediol | — | — | 1.2 | — | — | — | — | — | — | — | 1.2 | — | — | — | — | — | — | — |
| decyl-glyceryl ether | — | — | — | 1.2 | — | — | — | — | — | — | — | 1.2 | — | — | — | — | — | — |
| octyl glyceryl ether) | — | — | — | — | 1.2 | — | — | — | — | — | — | — | 1.2 | — | — | — | — | — |
| decyl glycidyl ether | — | — | — | — | — | 1.2 | — | — | — | — | — | — | — | 1.2 | — | — | — | — |
| octyl glycidyl ether | — | — | — | — | — | — | 1.2 | — | — | — | — | — | — | — | 1.2 | — | — | — |
| hexyl-1,3-dioxolane | — | — | — | — | — | — | — | 1.2 | — | — | — | — | — | — | — | 1.2 | — | — |
| octyl-1-3-dioxolane | — | — | — | — | — | — | — | — | 1.2 | — | — | — | — | — | — | — | 1.2 | — |
| decyl-1,3-dioxolane | — | — | — | — | — | — | — | — | — | 1.2 | — | — | — | — | — | — | — | 1.2 |
| Sita Foam Vol., ml | 94 | 102 | 110 | 105 | 105 | 99 | 106 | 108 | 108 | 99 | 122 | 112 | 111 | 114 | 111 | 114 | 121 | 101 |

Example 4 demonstrates that at lower total anionic concentrations, the undecyl-based surfactants are better than the lauryl surfactants. The family of co-surfactants improves the lather profiles of both the lauryl family and the undecyl-based family. The undecyl-based systems with co-surfactants at similar compositions are superior in flash lather.

*This example was carried out at room temperature (25° C.).

Example 5—Comparative Shampoo Formulations Examples and Switch Lather Profiles

Method

The switch lather test method is designed to evaluate the lather ease and volume for shampoo products. Switches of Asian virgin hair, flat construction, 15 g/25.4 cm (10 inches), are treated uniformly with 0.1 g of artificial sebum from hexane solution to provide a realistic soil level. In the lather evaluation the switch is first wet with tap water (37.8° C. (100° F.), 7-10 gpg hardness) and deliquored to a water content of 1 g $H_2O$/1 g hair. 0.75 ml of product is applied to the center of the switch; the lower portion of the switch is then rubbed over the product on the hair with 5 strokes in circular motion to distribute the product evenly. This is followed by 40 strokes with a back and forth motion. Lather ease is determined by the number of strokes required for lather to bloom.

After the 40, back and forth, strokes are completed the lather is collected from the operators gloves and placed into a graduated cylinder. The lather remaining in the hair is gathered in one downward stroke (squeeging) and is added to the initial amount. The total lather volume is recorded.

Three runs are made on each test product and the mean of the three values is calculated and used to represent the lather volume per treatment. High (Typical Clarifying Shampoo Formulation) and mid-range (Typical Conditioning Shampoo Formulation) market products are typically included as benchmark controls.

This test method represents a more realistic measure of in-use lather performance for a shampoo as actual human hair fibers with representative levels of sebum are the substrate for lather generation. It also assesses lather stability as the foam is collected and its volume is measured. An unstable foam would show a markedly reduced volume in these experiments. It also uses a 1:20 dilution of product which is representative of usage conditions at the stressed concentration end of actual consumer usage. The control prototype (8:4:1.2, SLS, SLE(3)S, CMEA, without additional conditioning ingredients (cationic polymer, silicone, organic oils)) exhibits a lather profile typical of a conditioning shampoo, which typically has higher total anionic surfactant and co-surfactant levels. As such it is a representative bench mark.

Formulations

The following example are Typical Clarifying Shampoo Formulation which generally provide the highest lather volume profiles. Evaluations are conducted according to the switch lather test method employing a Typical Clarifying Shampoo Formulation as a high control. A Typical Conditioning Shampoo Formulation is used as a mid-range control that is typical of a conditioning shampoo. The relative volumes produced are indexed to this control. The typical difference between these products is a 30% higher lather volume for Typical Clarifying Shampoo Formulation.

TABLE 4

Typical Clarifying Shampoo Formulation

| Raw Material | 36% (wt./wt.) |
|---|---|
| SLE3S | 7.0000 |
| tetrasodium EDTA | 0.1400 |
| Citric Acid (Anhy.) | 1.1100 |
| Sodium Citrate (dihydrate) | 0.0000 |
| Cocamide MEA | 0.5000 |
| Methyl chloroisothiazolinone and methyl isothiazolinone (Kathon CG) | 0.0300 |
| SLS | 7.0000 |
| 1,3-bis(hydroxymethyl)-5,5-dimethylimidazolidine-2,4-dione (DMDM Hydantoin) | 0.1000 |
| cocoamidopropyl betaine | 2.0000 |
| Cocamide MEA | 0.5 |
| NaCl | 0.7000 |
| Perfume | 0.4600 |
| Distilled Water | To 100.0000 |

TABLE 5

Typical Conditioning Shampoo Formulation

| Ingredient | 37 Wt. % |
|---|---|
| Distilled Water | To 100 |
| Polyquaternium 10 (Ucare Polymer LR-400) | 0.5000 |
| Ammonium Laureth Sulfate (AE3S) | 10.0000 |
| Nonionic poly(ethylene oxide) polymer (Polyox - Stock Soln.*) | 2.0000 |
| Citric Acid (50% Soln.) | 0.0800 |
| Hydrogenated polydecene (Puresyn 6) | 0.3000 |
| Trimethylolpropane tricaprylate/tricaprate (Puresyn 3E20) | 0.1000 |
| Sodium Chloride | 0.5500 |
| Sodium Benzoate | 0.2500 |
| Disodium EDTA | 0.1270 |
| Sodium Citrate (dihydrate) | 0.4520 |
| Cetyl Alcohol | 0.9000 |
| CMEA | 0.9000 |
| EGDS (ethylene glycol distearate) | 1.5000 |
| Methyl chloroisothiazolinone and methyl isothiazolinone (Kathon CG) | 0.0333 |
| Ammonium Lauryl Sulfate (ALS) | 6.0000 |
| Panthenol | 0.0536 |
| Panthenyl Ethyl Ether | 0.0300 |
| Perfume | 0.5500 |
| Silicone Emulsion | 1.3500 |
| Total | 25.6759 |
| Nonionic poly(ethylene oxide) polymer Polyox Premix | 24.3000 |
| Methyl chloroisothiazolinone and methyl isothiazolinone (Kathon CG) | 0.0330 |
| Distilled Water | To 100 |

*Polyox Premix Formulation

Table 6 below is a comparison of undecyl to lauryl chain lengths with various co-surfactants in a clarifying shampoo. *Typical Clarifying Shampoo Formulation (formula 38) results are those presented in the first data column above.

TABLE 6

| | 38 Wt % | 39 Wt % | 40 Wt % | 41 Wt % | 42 Wt % | 43 Wt % | 44 Wt % | 45 Wt % | 46 Wt % | 47 Wt % | 48 Wt % | 49 Wt % | 50 Wt % | 51 Wt % | 52 Wt % | 53 Wt % | 54 Wt % | 55 Wt % |
|---|---|---|---|---|---|---|---|---|---|---|---|---|---|---|---|---|---|---|
| Sodium Lauryl Sulfate | 7 | 0 | — | — | — | — | 6 | 7 | — | 7 | 2 | — | — | — | — | — | — | — |
| Sodium Laureth Sulfate | 7 | 0 | — | — | — | — | — | — | 7 | — | — | — | — | — | — | — | — | — |
| Sodium Undecyl Sulfate | — | 6 | 6 | 12 | — | 7 | — | — | — | — | — | — | — | — | — | — | — | — |
| Sodium Undeceth 1 Sulfate | — | 6 | 6 | — | 12 | 7 | 6 | — | 7 | — | 5 | — | — | 12 | 8 | — | — | — |
| Ammonium Undecyl Sulfate | — | — | — | — | — | — | 7 | — | 5 | 5 | — | — | — | — | 4 | — | — | — |
| Ammonium Undeceth 1 Sulfate | — | — | — | — | — | — | — | — | — | — | — | 12 | 8 | — | — | — | 12 | 8 |
| Cocomonoethanol Amide | 0.5 | 0.5 | 0.5 | 0.5 | 0.5 | 0.5 | 0.5 | 0.5 | 0.5 | 0.5 | 0.5 | 1 | 1 | — | — | — | — | — |
| Cocoamidopropyl Betaine | 2 | 1 | 2 | 1 | 1 | 2 | 1 | 2 | 2 | 2 | 2 | — | — | — | — | — | — | — |
| 1,2-decanediol | — | — | — | — | — | — | — | — | — | — | — | — | — | 1 | 1 | 1 | 1 | 1 |
| Switch Lather Index | 1.3 | 1.3 | 1.7 | 1.3 | 1.6 | 1.9 | 1.6 | 2 | 1.8 | 2 | 2 | 1.7 | 1.4 | 1.8 | 1.8 | 1.4 | 1.8 | 1.7 |

This testing confirms that in undecyl-based clarifying shampoo bases, both sodium and ammonium forms, provide equivalent lather volumes at lower concentrations compared to lauryl-based shampoo bases. Furthermore, it also demonstrates that undecyl-based compositions can be used at equivalent concentrations (with co-surfactant) to provide exceptional lather volumes compared to lauryl-based shampoo bases. Additionally, in undecyl-based systems, lower co-surfactant concentrations can be used to provide at least equivalent lather volumes. Furthermore, compositions with the co-surfactant 1,2-decanediol, versus conventional co-surfactants, also provide exceptional lather at markedly reduced levels.

Example 6—Switch Lather of a Conditioning Shampoo

The formula for a Typical Conditioning Shampoo Formulation used for this example is the same as that set forth in Example 5 above.

Table 7 below is a comparison of undecyl to lauryl chain length surfactant systems with various co-surfactants in a conditioning shampoo base surfactant system. The control surfactant system is formula 56. Formula 56 has a lather profile equal to the described conditioning shampoo and allows relative comparisons of surfactant systems without conditioning agents.

Anionic Surfactants

Example 6 testing confirms the lathering superiority of the undecyl-based surfactants vs. their lauryl-based counterparts on hair switches with sebum. A selection of various co-surfactants confirms their lather-boosting functionality in these formulations. The selection of co-surfactants above provide exceptional lather profiles vs. CMEA containing compositions.

Example 7

The formula for a Typical Conditioning Shampoo Formulation used for this example is the same as that set forth in Example 5 above.

Table 8 below is a comparison of undecyl to lauryl chain length surfactant systems with various co-surfactants in a conditioning shampoo base surfactant system. The control surfactant system is formula 69. It has a lather profile equal to the described conditioning shampoo and allows relative comparisons of surfactant systems without conditioning agents.

TABLE 7

|  | 56 Wt. % | 57 Wt. % | 58 Wt. % | 59 Wt. % | 60 Wt. % | 61 Wt. % | 62 Wt. % | 63 Wt. % | 64 Wt. % | 65 Wt. % | 66 Wt. % | 67 Wt. % | 68 Wt. % |
|---|---|---|---|---|---|---|---|---|---|---|---|---|---|
| Sodium Lauryl Sulfate | 8 | — | — | — | — | — | — | — | — | — | — | — | — |
| Sodium Laureth Sulfate | 4 | — | — | — | — | — | — | — | — | — | — | — | — |
| Sodium Undecyl Sulfate | — | 8 | 8 | 8 | 8 | 8 | — | — | 12 | 8 | — | — | — |
| Sodium Undeceth 1 Sulfate | — | 4 | 4 | 4 | 4 | 4 | — | — | — | 4 | — | — | — |
| Ammonium Undecyl Sulfate | — | — | — | — | — | — | 12 | 8 | — | — | 12 | 8 | — |
| Ammonium Undeceth 1 Sulfate | — | — | — | — | — | — | — | 4 | — | — | — | 4 | 12 |
| Cocomonoethanol Amide | 1.2 | 1.2 | — | — | — | — | 1 | 1 | — | — | — | — | — |
| 1,2-decanediol | — | — | 1.2 | — | — | — | — | — | 1 | 1 | 1 | 1 | 1 |
| decylglycerylether diol | — | — | — | 1.2 | — | — | — | — | — | — | — | — | — |
| octylglycerylether diol | — | — | — | — | 1.2 | — | — | — | — | — | — | — | — |
| decylglycerylether epoxide | — | — | — | — | — | 1.2 | — | — | — | — | — | — | — |
| Switch Lather Index | 1 | 1.7 | 2.1 | 1.8 | 1.6 | 1.7 | 1.7 | 1.4 | 1.8 | 1.8 | 1.8 | 1.7 | 1.4 |

Switch Lather, Conditioning Shampoo Surfactant Base

TABLE 8

|  | 69 Wt. % | 70 Wt. % | 71 Wt. % | 72 Wt. % | 73 Wt. % | 74 Wt. % | 75 Wt. % | 76 Wt. % | 77 Wt. % |
| --- | --- | --- | --- | --- | --- | --- | --- | --- | --- |
| Sodium Lauryl Sulfate | 8 | — | — | — | — | — | — | — | — |
| Sodium Laureth Sulfate SLE(3)S | 4 | — | — | — | — | — | — | — | — |
| Undecyl sulfate | — | 8 | 8 | 8 | 8 | 8 | 8 | 8 | 8 |
| Undeceth(1) Sulfate | — | 4 | 4 | 4 | 4 | 4 | 4 | 4 | 4 |
| Co-surfactants |  |  |  |  |  |  |  |  |  |
| 1,2-decanediol | — | — | 1.2 | — | — | — | — | — | — |
| decylglycerylether | — | — | — | 1.2 | — | — | — | — | — |
| octylglycerylether | — | — | — | — | 1.2 | — | — | — | — |
| decylglycidol | — | — | — | — | — | 1.2 | — | — | — |
| octylglycidol | — | — | — | — | — | — | 1.2 | — | — |
| octyl-1,3 dioxolane | — | — | — | — | — | — | — | 1.2 | — |
| decy-1,3 dioxolane | — | — | — | — | — | — | — | — | 1.2 |
| CMEA | 1.2 | 1.2 |  |  |  |  |  |  |  |
| Switch Lather Index | 1 | 1.7 | 2.1 | 1.8 | 1.6 | 1.7 | 1.5 | 1.4 | 1.3 |

Additional evaluations of co-surfactants indicates that they provide improved lather profiles over the control product and would be effective shampoo surfactant bases.

Example 8

Hair Lather Rinsing Method

The hair lather rinse method is designed to assess the rinsing time for shampoo products under median usage conditions of concentration, temperature, water flow, and water quality. 4 gram, 8 inch switches are prewet for 10 seconds with water at 37.8° C. (100° F.), 7-10 gpg hardness at a flow rate of 0.65-0.70 gpm. The excess water is squeezed out to achieve a water content of 1 g H₂O to 1 g of hair. 0.4 g of shampoo is applied to the hair switch at the middle, the switch is folded in the middle and it is worked in a back and forth motion for 30 seconds to generate lather. An evaluation of the lather amount and texture is recorded. The switch is unfolded and the water applied to the switch. A stop watch is started simultaneously and the time recorded for complete disappearance (water run clear) of lather on the switch. Each product is tested in triplicate and the average rinsing time determined. A typical test will analyze up to ten prototype products and an internal control is always included, e.g. Typical Conditioning Shampoo Formulation (Table 4, formula 36) and Typical Clarifying Shampoo Formulation (Table 5, formula 37).

TABLE 9

| | | | | | Rinsing Data | | | | | |
| --- | --- | --- | --- | --- | --- | --- | --- | --- | --- | --- |
| Product | 78 Wt. % | 79 Wt. % | 80 Wt. % | 81 Wt. % | 82 Wt. % | 83 Wt. % | 84 Wt. % | 85 Wt. % | 86 Wt. % | 87 Wt. % |
| SLS | 11.5 | 1.5 | 1.5 | 4.5 | 7.5 | 1.5 | 1.5 | 4.5 | 7 | 6 |
| SLE(3)S | — | 10 | — | 7 | 4 | 4 | — | — | 7 | 10 |
| C11S | — | — | 10 | — | — | 6 | — | — | — | — |
| C11E(1)S | — | — | — | — | — | — | 10 | 7 | — | — |
| SLE(1)S | — | — | — | — | — | — | — | — | — | — |
| CMEA | 1.2 | 1.2 | 1.2 | 1.2 | 1.2 | 1.2 | 1.2 | 1.2 | 0.5 | 1.5 |
| CAPB |  |  |  |  |  |  |  |  | 2 |  |
| Benefit Agents |  |  |  |  |  |  |  |  |  |  |
| Pearlizer-EGDS | 1.5 | 1.5 | 1.5 | 1.5 | 1.5 | 1.5 | 1.5 | 1.5 | — | 1.5 |
| Silicone emulsion | 1.35 | 1.35 | 1.35 | 1.35 | 1.35 | 1.4 | 1.4 | 1.4 | — | 1.4 |
| cationic polymer | 0.5 | 0.5 | 0.5 | 0.5 | 0.5 | 0.5 | 0.5 | 0.5 | — | 0.5 |
| preservatives, pH control, etc. | To 100. | To 100 | To 100 | To 100 | To 100 | To 100 | To 100 | To 100 | To 100 | To 100 |
| Switch lather index | 1.3 | 0.75 | 1.2 | 0.86 | 1 | 1 | 1.2 | 1.3 | 1.3 | 1 |
| Switch Rinse Time, sec | 10 | 11 | 8 | 9.9 | 10 | 8.2 | 8.4 | 8 | 8.1 | 13 |

Product 9 = Clarifying high control
Product 10 = High conditioning control

From Table 9 above, formula 80's rinse time shows that the use of undecyl-based surfactants provides acceptable target rinse time with no compromise in lather, versus lauryl-based systems (formulas 78, 79, 81, and 82). Furthermore, in formulas 83-85, the addition of undecyl-based surfactants to lauryl-based systems decreases rinse time vs. lauryl-only (78, 79, 81, and 82). This example thus demonstrates that undecyl-derived conditioning products with switch lather indexes essentially equal to a high conditioning control have rinsing times equal to a fast rinsing clarifying shampoo.

Example 8—Pump Foamer Products

The following examples in Table 10 demonstrate that high performing hand wash products can be produced from the undecyl-based surfactants. The key to them dispensing as luxurious foam is to keep the viscosity of the formulation below 60 cps. The undecyl-based surfactants are key to achieving this result. Examples of both shampoo and hand wash formulations follow. Standard lauryl-based surfactants alone cannot achieve this low viscosity without solvent and hydrotrope.

TABLE 10

Hand Wash Formulations

| Ingredients | 88 Wt. % | 89 Wt. % |
|---|---|---|
| Undecyl sulfate | 36.5 | 30 |
| Cocobetaine | | 1.0 |
| Hand lather performance | Excellent | Excellent |

Example 9—Conditioning Body Washes

The following example described in Table 11 shows a non-limiting example of the structured surfactant composition of the present invention comprising sodium undecyl sulfate.

TABLE 11

Structured Surfactant with Sodium Undecyl Sulfate

| | Composition 90 Wt. % |
|---|---|
| Sodium Lauroamphoacetate (Miranol L-32, Rhodia Inc.) | 5.06 |
| Sodium Trideceth Sulfate (sulfated from Iconol TDA-3 (BASF Corp.) to >95% sulfate) | 8.48 |
| Sodium Undecyl Sulfate | 8.48 |
| Trideceth-3 (Iconal TDA-3 from BASF Corp.) | 2 |
| Sodium Chloride | 4.75 |
| Guar hydroxypropyltrimonium chloride (N-Hance 3196 Polymer) | 0.6 |
| Polyethyleneoxide (Polyox WSR301) | 0.15 |
| Xanthan gum (Keltrol 1000, Kelco Corp.) | 0.22 |
| Methyl chloro isothiazolinone and methyl isothiazolinone (Kathon CG, Rohm & Haas) | 0.033 |
| EDTA (Dissolvine NA 2x) | 0.15 |
| Sodium Benzoate | 0.2 |
| Citric Acid, titrate | pH = 5.7 ± 0.2 |
| Perfume | 2.0 |
| Water | To 100 |
| Lamellar Phase Volume through Ultracentrifugation Test Method | 83% |
| Zero-Shear Viscosity through Rheology Test Method | 7884 Pa · S. |

The compositions described above in Table 11 can be prepared by conventional formulation and mixing techniques. Prepare the structured surfactant phase composition by first adding citric acid into water at 1:3 ratios to form a citric acid premix. Prepare a polymer premix by adding Polyox WSR301 and Xanthan Gum into Trideceth-3. Then, add the following ingredients into the main mixing vessel in the following sequence with continuous agitation: water, sodium chloride, N-Hance polymer, sodium lauroamphoacetate, polymer premix with Trideceth-3, sodium trideceth sulfate, sodium undecyl sulfate, sodium benzoate, and Disodium EDTA. Add citric acid premix to adjust pH to 5.7±0.2. Add perfume and Kathon CG while continuing to agitate until homogeneous.

The structured surfactant phase contains about 83% lamellar phase as measured through ultracentrifugation test method as disclosed herein. The structured surfactant phase comprising undecyl sulfate has a zero shear viscosity of about 7884 PaS as measured by the rheology method as disclosed herein.

The following example described in Table 12 shows a non-limiting example of the multiphase composition the present invention comprising sodium undecyl sulfate.

TABLE 12

Multiphase Composition with Sodium Undecyl Sulfate

| | Composition Wt. % |
|---|---|
| Phase 1: | |
| Structured Surfactant Phase from Table 11 | 55% |
| Phase 2: | |
| Lipid Phase with G2218 Petrolatum and Hydrobrite 1000 Mineral Oil at 70:30 Ratio (G2218 Petrolatum and Hydrobrite 1000 Mineral Oil obtained from Sonneborn) | 45% |

The lipid phase is prepared by heating the G2218 Petrolatum and Hydrobrite 1000 Mineral Oil to 180° C. Then petrolatum and mineral oil to the mixing vessel and agitation. Then cool the mixture down to about 45° C. Add the lipid phase to the structured surfactant phase with agitation until homogeneous. The multiphase phase composition is placed at 49° C. for 10 days. The multiphase composition is stable if the multiple phases still remain.

Additional Exemplary Anti-Dandruff Formulations

TABLE 13

| Ingredients | 91 Wt % | 92 Wt % | 93 Wt % |
|---|---|---|---|
| SLE(1)S | 9.20 | 9.20 | 7.50 |
| SC11S | 3.4 | 3.4 | 3 |
| SLS | 1.5 | 1.5 | 1.5 |
| Cocobetaine | 2 | 2 | 2.5 |
| Zinc pyrithione | 1.5 | 1.5 | 1 |
| ZnCO$_3$ | 1.5 | 0.15 | 0.15 |
| Guar | 0.25 | 0.25 | 0.2 |
| EGDS | 1.5 | 1.5 | 1.5 |
| LP-silicone | 0 | 0 | 1.25 |
| Perfume, minors, water | To 100 | To 100 | To 100 |
| Lather PerformanceIndexed to Clarifying | 1.3 | 1.4 | 1.4 |
| Wet Conditioning | N/A | N/A | ++ |
| Dry Conditioning | N/A | N/A | ++ |

TABLE 14

|  | 94 | 95 | 96 | 97 | 98 | 99 | 100 | 101 | 102 |
|---|---|---|---|---|---|---|---|---|---|
| SLE(3)S | — | 6 | — | — | — | — | 1 | 2 | 12 |
| SLS | — | 1.5 | 1.5 | — | 1.25 | — | — | 1.5 | — |
| SLE(1)S | 6 | — | 14 | 7 | 15 | 6 | 8 | 8.5 | — |
| C11S | 3 | 7 | 4.5 | 5 | 3 | 12 | 3 | 6 | 2 |
| CAPB | — | — | — | — | 2.0 | — | 0.5 | 1.0 | 2 |
| CMEA | — | 0.8 | — | 0.5 | 0.8 | — | — | 0.8 | — |
| CocoB | 2 | — | 1.8 | .1 | — | 1.0 | — | — | — |
| Cetyl alcohol | — | 0.5 | — | — | — | .6 | 0.9 | — | — |
| Guar | 0.15 | — | 0.4 | 0.6 | 0.1 | — | 0.1 | 0.2 | — |
| PQ-10 | — | 0.2 | — | — | — | 0.2 | — | — | 0.2 |
| AM:Triquat | 0.20 | 0.1 | — | — | — | — | — | 0.1 | 0.1 |
| DADMAC | — | — | 0.1 | — | — | 0.3 | — | — | — |
| Zinc Pyrithione | 1 | 1 | 0.5 | 1 | 2 | 1 | 0.5 | 1 | 1 |
| Zinc Carbonate | 1.6 | 1.6 | 1.6 | 1.6 | 3.2 | 1.6 | 1.6 | 1.6 | 1.6 |
| EGDS | 1.5 | 1.5 | 1.5 | 1.25 | 1.5 | 1.25 | — | 1.5 | — |
| LP Silicone | 2.1 | 2.1 | 2.0 | 0.7 | 1.5 | 3.0 | 0.5 | — | — |
| Amino-silicone | — | — | — | — | — | — | — | 1.0 | — |
| Silicone micro-emulsion | — | — | — | — | — | — | — | — | 0.5 |
| Perfume, Finishing Agents and water | To 100 | To 100 | To 100 | To 100 | To 100 | To 100 | To 100 | To 100 | To 100 |

Yield Stress and Zero Shear Viscosity Method:

The Yield Stress and Zero Shear Viscosity of a phase of the present composition, can be measured either prior to combining in the composition, or after combining in the composition by separating the phase by suitable physical separation means, such as centrifugation, pipetting, cutting away mechanically, rinsing, filtering, or other separation means.

A controlled stress rheometer such as a TA Instruments AR2000 Rheometer is used to determine the Yield Stress and Zero Shear Viscosity. The determination is performed at 25° C. with the 4 cm diameter parallel plate measuring system and a 1 mm gap. The geometry has a shear stress factor of 79580 $m^{-3}$ to convert torque obtained to stress. Serrated plates can be used to obtain consistent results when slip occurs.

First a sample of the phase is obtained and placed in position on the rheometer base plate, the measurement geometry (upper plate) moving into position 1 mm above the base plate. Excess phase at the geometry edge is removed by scraping after locking the geometry. If the phase comprises particles discernible to the eye or by feel (e.g., beads) which are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The determination is performed via the programmed application of a continuous shear stress ramp from 0.1 Pa to 1,000 Pa over a time interval of 4 minutes using a logarithmic progression, i.e., measurement points evenly spaced on a logarithmic scale. Thirty (30) measurement points per decade of stress increase are obtained. Stress, strain and viscosity are recorded. If the measurement result is incomplete, for example if material flows from the gap, results obtained are evaluated and incomplete data points excluded. The Yield Stress is determined as follows. Stress (Pa) and strain (unitless) data are transformed by taking their logarithms (base 10). Log(stress) is graphed vs. log(strain) for only the data obtained between a stress of 0.2 Pa and 2.0 Pa, about 30 points. If the viscosity at a stress of 1 Pa is less than 500 Pa-sec but greater than 75 Pa-sec, then log(stress) is graphed vs. log(strain) for only the data between 0.2 Pa and 1.0 Pa, and the following mathematical procedure is followed. If the viscosity at a stress of 1 Pa is less than 75 Pa-sec, the zero shear viscosity is the median of the 4 highest viscosity values (i.e., individual points) obtained in the test, the yield stress is zero, and the following mathematical procedure is not used. The mathematical procedure is as follows. A straight line least squares regression is performed on the results using the logarithmically transformed data in the indicated stress region, an equation being obtained of the form:

$$\text{Log(strain)} = m*\text{Log(stress)} + b \quad (1)$$

Using the regression obtained, for each stress value (i.e., individual point) in the determination between 0.1 and 1,000 Pa, a predicted value of log(strain) is obtained using the coefficients m and b obtained, and the actual stress, using Equation (1). From the predicted log(strain), a predicted strain at each stress is obtained by taking the antilog (i.e., $10^x$ for each x). The predicted strain is compared to the actual strain at each measurement point to obtain a % variation at each point, using Equation (2).

$$\% \text{ variation} = 100*(\text{measured strain} - \text{predicted strain})/\text{measured strain} \quad (2)$$

The Yield Stress is the first stress (Pa) at which % variation exceeds 10% and subsequent (higher) stresses result in even greater variation than 10% due to the onset of flow or deformation of the structure. The Zero Shear Viscosity is obtained by taking a first median value of viscosity in Pascal-seconds (Pa-sec) for viscosity data obtained between and including 0.1 Pa and the Yield Stress. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

The Shear Index (n) and Consistency Value (K):

The Shear Index (n) and Consistency Value (K) are known and accepted means for reporting the viscosity profile of materials having a viscosity that varies with applied shear rate using a Power Law model. The term "Consistency value" or "K" as used herein is a measure of viscosity and is used in combination with Shear Index, to define viscosity for materials whose viscosity is a function of shear rate. The measurements of Consistency value and Shear Index are made at 25° C. The units for "Consistency value" or "K" are Pascal seconds. The units for "Shear Index" are dimensionless.

Viscosity of a phase can be measured by applying a shear stress and measuring the shear rate using a rheometer, such as a TA Instruments AR2000 (TA Instruments, New Castle, Del., USA 19720). Viscosity is determined at different shear rates in the following manner. First, the benefit phase is obtained. If there exists more than one distinct (immiscible, e.g.) benefit phase in the composition, such as for example a silicone oil phase and a hydrocarbon phase, they are preferably prepared separately and/or separated from each other, and evaluated separately from each other, although certain benefit phases which are mixtures such as emulsions can be evaluated as mixtures, in addition to evaluating the individual benefit phases individually.

For measurement, a 40 mm diameter parallel plate geometry with a gap of 1 mm is used unless there are particles greater than 0.25 mm, in which case a gap of 2 mm is used. The rheometer uses standard parallel plate conventions to report shear rate at the edge as shear rate of the test; and converts torque to stress using the factor $2/(\pi R^3)$. Using a spatula, a sample comprising a small excess of the benefit phase is loaded onto the rheometer base plate which is at 25° C., the gap is obtained, and excess composition outside the top measurement geometry is removed, locking the top plate in position during the removal of excess sample. The sample is equilibrated to the base plate temperature for 2 minutes. A preshear step is performed comprising 15 seconds of shear at a shear rate of 50 inverse seconds (1/sec). As is known to one skilled in the art, the shear rate with a parallel plate geometry is expressed as the shear rate at the edge, which is also the maximum shear rate. After the preshear step, the measurement is performed, which comprises ramping the stress from 10 Pa to 1,000 Pa over a 2.0 minute interval at 25° C., while collecting 60 viscosity data points, in an evenly spaced linear progression. A shear rate of at least 500 l/seconds is obtained in the test, or the test is repeated with a fresh sample of the same component with a higher final stress value, maintaining the same rate of stress increase per time, until a shear rate of at least 500 l/sec is obtained during the measurement period. During the measurement, observe the sample to make certain the area under the top parallel plate is not evacuated of sample at any edge location during the measurement, or the measurement is repeated until a sample remains for the duration of the test. If after several trials a result cannot be obtained due to sample evacuation at the edge, the measurement is repeated leaving an excess reservoir of material at the edge (not scraping). If evacuation still cannot be avoided, a concentric cylinder geometry is used with a large excess of sample to avoid air pockets during loading. The results are fitted to the power law model by selecting only the data points between 25-500 l/sec shear rate, viscosity in Pa-s, shear rate in 1/sec, and using a least squares regression of the logarithm of viscosity vs. the logarithm of shear rate to obtain values of K and n according to the Power Law equation:

$$\mu = K(\gamma')^{(n-1)}$$

The value obtained for the log-log slope is (n−1) where n is the Shear Index and the value obtained for K is the Consistency Value, expressed in units of in Pa-s.

Ultracentrifugation "Third-Phase" Method for Determining Structured Surfactant Stability:

The Ultracentrifugation "Third-Phase" Method is used to determine structured surfactant phase stability in a personal care composition.

The method involves separation of the composition through ultracentrifugation into separate but distinguishable layers. The personal care composition of the present invention can have multiple distinguishable layers, for example a non-structured surfactant layer, an opaque structured surfactant layer, a clear "third-phase" layer, and benefit phase layers.

The rapid stability aging protocol is set as follow. Prepare a lipid blend by heating a vessel to 180° F. (82.2° C.) and add Petrolatum (Quidesa Petrolatum from Quidesa, Mexico) and Hydrobrite 1000 White Mineral Oil (from WITCO, USA) at 65:35 weight ratio. Cool the vessel to 110° F. (43.3° C.) with slow agitation (200 rpm). Stop agitation and cool the vessel to ambient temperature overnight. Add 36 grams of lipid blend (65/35 Pet/MO) to about 44 grams of the structured surfactant composition. Mix the surfactant and lipid together using a spatula for 5 minutes. Place the mixed sample at 120° F. (48.9° C.) for 10 days. After rapid aging stability testing, transfer about 4 grams of the composition into a Beckman Centrifuge Tube (11×60 mm). Place the centrifuge tube in a Beckman LE-80 Ultracentrifuge and operate the Ultracentrifuge under the following conditions: 50,000 rpm, 2 hours, and at 40° C.

Figure 2:
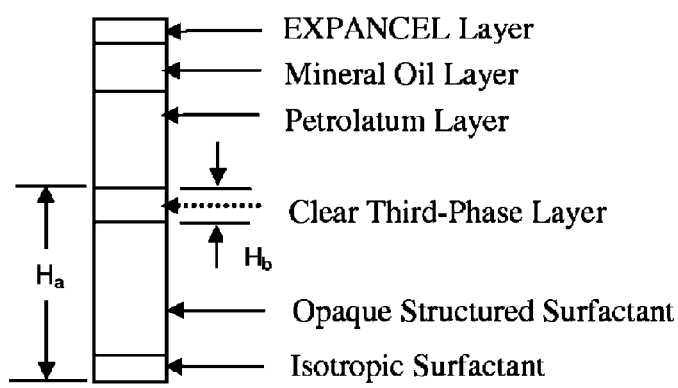
FIG. 2 shows the method to determine the third-phase volume by measuring the height of various surfactant phases of an exemplified cleansing.

After Ultracentrifugation, determine the third-phase volume by measuring the height of various surfactant phases using an Electronic Digital Caliper (within 0.01 mm) as shown in FIG. 2. An example is shown in FIG. 2 for a cleansing composition comprising EXPANCEL® microspheres, petrolatum, mineral oil and a structured surfactant phase.

When a density modifier such as EXPANCEL® hollow microspheres is used, the very top layer primarily comprises the EXPANCEL® microspheres. The second layer from the top is the clear mineral oil layer. The third layer from the top is the petrolatum layer. The layers below the petrolatum layers contain aqueous surfactant and are characterized as follows: $H_a$ is the height of all the aqueous and/or aqueous surfactant layers and $H_b$ is the height of the clear "third-phase" layer just below the petrolatum layer. It is important to record the readings within 30 minutes after the Ultracentrifugation is finished to minimize material migration. The third phase volume is calculated as: Third-phase Volume %=$H_b/H_a$*100%

Preferably, the structured surfactant composition comprises less than 5% "third-phase" volume after rapid aging protocol. More preferably, the structured surfactant composition comprises less than 2% "third-phase" volume after rapid aging protocol. Most preferably, the structured surfactant composition comprises less than 1% "third-phase" volume after rapid aging protocol.

Method for Assessment of Zinc Lability in Zinc-Containing Products

Zinc lability is a measure of the chemical availability of zinc ion. Soluble zinc salts that do not complex with other species in solution have a relative zinc lability, by definition, of 100%. The use of partially soluble forms of zinc salts and/or incorporation in a matrix with potential complexants generally lowers the zinc lability substantially below the defined 100% maximum.

Zinc lability is assessed by combining a diluted zinc-containing solution or dispersion with the metallochromic dye xylenol orange (XO) and measurement of the degree of color change under specified conditions. The magnitude of color formation is proportional to the level of labile zinc. The procedure developed has been optimized for aqueous surfactant formulations but may be adapted to other physical product forms as well.

A spectrophotometer is used to quantify the color change at 572 nm, the wavelength of optimum color change for XO. The spectrophotometer is set to zero absorbance at 572 nm utilizing a product control as close in composition to the test product except excluding the potentially labile form of zinc. The control and test products are then treated identically as follows. A 50 µl product sample is dispensed into a jar and 95 ml of deaerated, distilled water are added and stirred. 5 mL of a 23 mg/mL xylenol orange stock solution at pH 5.0 is pipetted into the sample jar; this is considered time 0. The pH is then adjusted to 5.50±0.01 using dilute HCl or NaOH. After 10.0 minutes, a portion of the sample is filtered (0.45µ) and the absorbance measured at 572 nm. The measured absorbance is then compared to a separately measured control to determine the relative zinc lability (zero TO 100%). The 100% lability control is prepared in a matrix similar to the test products but utilizing a soluble zinc material (such as zinc sulfate) incorporated at an equivalent level on a zinc basis. The absorbance of the 100% lability control is measured as above for the test materials. The relative zinc lability is preferably greater than about 15%, more preferably greater than about 20%, and even more preferably greater than about 25%.

Using this methodology, the below examples demonstrate a material (basic zinc carbonate) that has intrinsically high lability in an anionic surfactant system compared to one (ZnO) with low intrinsic lability.

TABLE 15

|  | Relative Zinc Lability (%) In Water | Relative Zinc Lability (%) In Simple Surfactant System[1] | Lability Benefit |
|---|---|---|---|
| Zinc Oxide | 86.3 | 1.5 | NO |
| Basic zinc carbonate | 100 | 37 | YES |

[1]Simple surfactant system: 6% sodium lauryl sulfate (SLS)

Particle Size Determination Method

Particle size analyses on zinc oxide and hydrozincite raw materials are done using the Horiba LA-910 Particle Size Analyzer. The Horiba LA-910 instrument uses the principles of low-angle Fraunhofer Diffraction and Light Scattering to measure the particle size and distribution in a dilute solution of particles. Samples of these two types of raw materials are pre-dispersed in a dilute solution of Lauryl Polyether Alcohol and mixed before introduction to the instrument. On introduction the sample is further diluted and allowed to circulate in the instrument before a measurement is taken. After measurement a calculation algorithm is used to process the data that results in both a particle size and distribution. D(50) is the median particle size or the particle size which corresponds to 50% of the amount of particles are below this size. D(90) is the particle size which corresponds to 90% of the amount of particles are below this size. D(10) is the particle size which corresponds to 10% of the amount of particles are below this size.

Using this methodology, the below examples demonstrate the relationship between particle size and relative zinc lability for basic zinc carbonate.

TABLE 16

| Source | As received/milled[1] | Particle Size (µ)[2] | Relative Zinc Lability (%) |
|---|---|---|---|
| Elementis | As received | 4.5 | 51.6 |
| Elementis | Milled | 1.0 | 67.1 |
| Brüggemann | As received | 4.5 | 56.9 |
| Brüggemann | Milled | 1.0 | 76.4 |

[1]Milling method
[2]Particle size Determination

Surface Area Methodology

Surface area analysis is done using the Micromeritics Auto Pore IV. The Micromeritics Auto Pore IV uses the principles of capillary law governing penetration of a non-wetting liquid, more specifically mercury, into small pores to measure the total pore surface area. This law is expressed by the Washburn equation:

$$D = (1/P) 4\gamma \cos \varphi$$

where D is pore diameter, P is the applied pressure, $\gamma$ the surface tension of mercury, and $\varphi$ the contact angle between the mercury and the sample. The Washburn equation assumes that all pores are cylindrical. Representative surface area measurements were conducted on basic zinc carbonate and are described below.

Results

TABLE 17

| Sample | Surface Area (m²/g) |
|---|---|
| Brüggemann Zinc Carbonate[1] | 50.57 |
| Elementis Zinc Carbonate[2] | 38.0 |

[1]Commercially available as Zinc Carbonate AC
[2]Commerically available as Zinc Carbonate Key to Abbreviations
ALS—Ammonium Lauryl Sulfate
ALE(3)S—Ammonium Laureth(3) Sulfate
AM:TRI—Polyquat 76
SLS—Sodium Lauryl Sulfate
SLE(1)S—Sodium Laureth(1) Sulfate
SLE(3)S—Sodium laureth(3) Sulfate
SLS w/ C10—Sodium Lauryl Sulfate with 20% Decylsulfate
C11S—Undecyl sulfate
C11E(1)—Undeceth(1) sulfate
CAPB—Cocoamidopropyl Betaine
CocoB—Cocobetaine
CMEA—Cocomonoethanolamide
EGDS—Etheylene Glycol Distearate
Guar—Hydroxypropyltrimonium Chloride (cationic polymer)
LP-Silicone—Large Particle (>20 um) silicone
DC 1872 or Micro Silicone 1872—Dow Corning Silicone Microemulsion PQ-10 Polyquat-10

PS 1:2:1—C13-C15 Paraffin Sulfonate
NSKKbrC12—Sodium salt of hydroxyethyl-2-dodecyl ether sulfate SCS—Sodium Cumene Sulfonate
Neo67S or Neodol 67 Sulfate—Mixture of Linear and Branched Hexadecyl and Heptadecyl Alcohol Sulfates
Neodol 23 Sulfate—Mixture of Linear and Branched Dodecyl and Tridecyl Alcohol Sulfates
Lial 23—Mixture of Linear and Branched Dodecyl and Tridecyl Alcohol Sulfates
ZPT—Zinc pyridinethione The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising a dermatologically acceptable carrier, and from about 3 wt % to about 40 wt % of at least one undecyl sulfate surfactant compound selected from the group consisting of:
    a) $R_1$—$O(CH_2CHR_3O)_y$—$SO_3M$;
    b) $CH_3$—$(CH_2)_z$—$CHR_2$—$CH_2$—$O(CH_2CHR_3O)_y$—$SO_3M$; and
    c) mixtures thereof;
    where $R_1$ represents $CH_3(CH_2)_{10}$, $R_2$ represents a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not=0, and M is a mono-valent or di-valent, positively-charged cation.

2. The personal care composition of claim 1, additionally comprising a beauty benefit agent selected from the group consisting of conditioning agents, scalp-care agents, colorants, rheology modifiers, and combinations thereof.

3. The composition of claim 1, wherein M is selected from the group consisting of ammonium, sodium, potassium, magnesium, triethanolamine cation, and mixtures thereof.

4. The composition of claim 1, further comprising from about 0.5 wt % to about 10 wt % of a co-surfactant selected from the group consisting of an amphoteric surfactant, a zwitterionic surfactant, a cationic surfactant, a nonionic surfactant, and mixtures thereof.

5. The composition of claim 4, wherein the co-surfactant is selected from the group consisting of: Cocomonoethanol Amide, Cocoamidopropyl Betaine, Laurylamidopropyl Betaine, Cocobetaine, lauryl betaine, lauryl amine oxide, sodium lauryl amphoacetate, and mixtures thereof.

6. The composition of claim 1, wherein the concentration of the undecyl sulfate surfactant compound is from about 3 wt % to about 37 wt %, and wherein the composition further comprises from about 3 wt % to about 37 wt % of at least one additional anionic surfactant.

7. The composition of claim 6, additionally comprising a co-surfactant selected from the group consisting of an amphoteric surfactant, a zwitterionic surfactant, a cationic surfactant, a nonionic surfactant, and mixtures thereof.

8. The composition of claim 1, having a viscosity of from about 3,000 cps to about 500,000 cps.

9. A personal care composition comprising a dermatologically acceptable carrier, and from about 5 wt % to about 15 wt % of at least one undecyl sulfate surfactant compound of the formula $R_1$—$O(CH_2CHR_3O)_y$—$SO_3M$, where $R_1$ represents $CH_3(CH_2)_{10}$, $R_3$ is H or $CH_3$, y is 0 to 7, the average value of y is about 1 when y is not=0, and M is a mono-valent or di-valent, positively-charged cation.

10. The personal care composition of claim 9, additionally comprising a beauty benefit agent selected from the group consisting of conditioning agents, scalp-care agents, colorants, rheology modifiers, and combinations thereof.

11. The composition of claim 9, wherein M is selected from the group consisting of ammonium, sodium, potassium, magnesium, triethanolamine cation, and mixtures thereof.

12. The composition of claim 9, further comprising from about 0.5 wt % to about 10 wt % of a co-surfactant selected from the group consisting of an amphoteric surfactant, a zwitterionic surfactant, a cationic surfactant, a nonionic surfactant, and mixtures thereof.

13. The composition of claim 12, wherein the co-surfactant is selected from the group consisting of: Cocomonoethanol Amide, Cocoamidopropyl Betaine, Laurylamidopropyl Betaine, Cocobetaine, lauryl betaine, lauryl amine oxide, sodium lauryl amphoacetate, and mixtures thereof.

14. A single phase, isotropic personal care composition comprising a dermatologically acceptable carrier, and from about 3 wt % to about 40 wt % of at least one undecyl sulfate surfactant compound selected from the group consisting of:
    a) $R_1$—$O(CH_2CHR_3O)_y$—$SO_3M$;
    b) $CH_3$—$(CH_2)_z$—$CHR_2$—$CH_2$—$O(CH_2CHR_3O)_y$—$SO_3M$; and
    c) mixtures thereof;
    where $R_1$ represents $CH_3(CH_2)_{10}$, $R_2$ represents a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not=0, and M is a mono-valent or di-valent, positively-charged cation.

15. The composition of claim 14, wherein M is selected from the group consisting of ammonium, sodium, potassium, magnesium, triethanolamine cation, and mixtures thereof.

16. The composition of claim 14, further comprising from about 0.5 wt % to about 10 wt % of a co-surfactant selected from the group consisting of an amphoteric surfactant, a zwitterionic surfactant, a cationic surfactant, a nonionic surfactant, and mixtures thereof.

17. A single phase, isotropic personal care composition comprising a dermatologically acceptable carrier, and from about 3 wt % to about 40 wt % of at least one undecyl sulfate compound of the formula $CH_3$—$(CH_2)_z$—$CHR_2$—$CH_2$—$O(CH_2CHR_3O)_y$—$SO_3M$, where $R_2$ represents a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not=0, and M is a mono-valent or di-valent, positively-charged cation.

18. The composition of claim 17 comprising from about 5 wt % to about 15 wt % of the at least one undecyl sulfate compound.

19. A personal care composition comprising a dermatologically acceptable carrier, and from about 3 wt % to about 40 wt % of at least one undecyl sulfate surfactant compound of the formula $R_1$—$O(CH_2CHR_3O)_y$—$SO_3M$, where $R_1$ represents $CH_3(CH_2)_{10}$, $R_3$ is H or $CH_3$, y is 0 to 7, the average value of y is about 1 when y is not=0, and M is a mono-valent or di-valent, positively-charged cation.

20. The composition of claim 19 wherein y is 0.

21. The composition of claim 7, wherein the co-surfactant is selected from the group consisting of: Cocomonoethanol Amide, Cocoamidopropyl Betaine, Laurylamidopropyl Betaine, Cocobetaine, lauryl betaine, lauryl amine oxide, sodium lauryl amphoacetate, and mixtures thereof.

22. The composition of claim 16, wherein the co-surfactant is selected from the group consisting of: Cocomonoethanol Amide, Cocoamidopropyl Betaine, Laurylamidopropyl Betaine, Cocobetaine, lauryl betaine, lauryl amine oxide, sodium lauryl amphoacetate, and mixtures thereof.

* * * * *